(12) United States Patent
Bandyopadhyay et al.

(10) Patent No.: US 8,901,317 B2
(45) Date of Patent: Dec. 2, 2014

(54) TRYPTAMINE DERIVATIVES, THEIR PREPARATION AND THEIR USE IN GASTROPATHY

(75) Inventors: Uday Bandyopadhyay, West Bengal (IN); Chinmay Pal, West Bengal (IN); Samik Bindu, West Bengal (IN); Susanta Sekhar Adhikari, West Bengal (IN)

(73) Assignees: Council of Scientific & Industrial Research, New Delhi (IN); University of Calcutta, Kolkata (IN)

( * ) Notice: Subject to any disclaimer, the term of this patent is extended or adjusted under 35 U.S.C. 154(b) by 0 days.

(21) Appl. No.: 13/822,463

(22) PCT Filed: Sep. 14, 2011

(86) PCT No.: PCT/IB2011/002129
§ 371 (c)(1),
(2), (4) Date: Apr. 15, 2013

(87) PCT Pub. No.: WO2012/035406
PCT Pub. Date: Mar. 22, 2012

(65) Prior Publication Data
US 2013/0197052 A1 Aug. 1, 2013

(30) Foreign Application Priority Data
Sep. 14, 2010 (IN) ............................ 2173/DEL/2010

(51) Int. Cl.
*C07D 209/16* (2006.01)
(52) U.S. Cl.
CPC .................................. *C07D 209/16* (2013.01)
USPC ............................ 548/491; 514/419; 514/415
(58) Field of Classification Search
None
See application file for complete search history.

(56) References Cited

U.S. PATENT DOCUMENTS

| | | | | |
|---|---|---|---|---|
| 5,122,535 | A * | 6/1992 | Fraschini et al. | 514/415 |
| 5,571,833 | A * | 11/1996 | Kruse et al. | 514/414 |
| 6,518,297 | B2 * | 2/2003 | Glennon et al. | 514/415 |
| 7,645,886 | B2 * | 1/2010 | Berens et al. | 548/485 |
| 2002/0103383 | A1 * | 8/2002 | Glennon et al. | 548/504 |

OTHER PUBLICATIONS

Yamazaki et al. Bioorganic & Medicinal Chemistry Letters vol. 19(15): 4178-4182 (2009).*
Shiumn-Jen Liaw et al.: "Beneficial role of melatonin on microcirculation in endotoxin-induced gastropathy in rats: possible implication in nitrogen oxide reduction", Journal of the Formosan Medical Association, vol. 101, No. 2, 2002, pp. 129-135.
Lewinsky A. et al.: "Influence of pineal indoleamines on the mitotic activity of gastric and colonic mucosa epithelial cells in the reat: interaction with omepreazole", vol. 10, 1991, pp. 104-108, N-acetyl-serotonine and melatonin.
Hui Li Zang et al.: "Antixidative compounds isolated from safflower (*Carthamus tinctorius*1.) oil cake", Chemical & Pharmaceutical Bulletin, Pharmaceutical Society of Japan, vol. 45, No. 12, 1997, pp. 1910-1914.
Andrianaivoravelona J. O. et al.: "A phenolic glycoside and N-(p-coumaroyl)-tryptamine from *Ravensara anisata*", Phytochemistry, Pergamon Press, GB, vol. 52, No. 6, 1999, pp. 1145-1148.
Shoeb M. et al.: "Montamine, a unique dimeric indole alkaloid, from the seeds of *Centaurea montana* (Asteraceae), and its in vitro cytotoxic activity against the CaCo2 colon cancer cells", Tetrahedron, Elsevier Science Publishers, Amsterdam, NL, vol. 62, No. 48, 2006, pp. 11172-11177.
Sarker S. D. et al.: "Indole alkaloids from the seeds of *Centaurea cyanus* (Asteraceae)", Phytochemistry, Pergamon Press, GB, vol. 57, No. 8, 2001, pp. 1273-1276.
Sungzong Kand & Jack Peter Green: "Resonance Constants and the Activities of Indolealkylamines on Stomach Muscle", Nature, vol. 222, 1969, pp. 794-795.
Nakai, Yu-Ya et al.: "Neucleophilic substitution reaction of N-(2(1-hydroxyindol-3-yl)ethyl]indole-3-acetamide and -1-hydroxyindole-3-acetamide"; Abstract; Database Accession No. 139:381325, (2003).
Yu-Ya Nakai et al.: "Neucleophilic substitution reaction of N-(2(1-hydroxyindol-3-yl)ethyl]indole-3-acetamide and -1-hydroxyindole-3-acetamide", Heterocycles, vol. 60, No. 7, 2003, pp. 1589-1600.
Wu, Bin et al.: "Synthesis and biological activity of N-substituted-3-indolylacetamide series as .alpha.1-adrenoceptor antagonists", Abstract XP-002664128; Database Accession No. 145:314749, (2004).
N. Duran et al.: "Biosynthesis of a trypanocide by chromobacterium violaceum", World Journal of Microbiology & Biotechnology, vol. 10, 1994, pp. 686-690.
International Preliminary Report on Patentability; PCT/IB2011/002129; Feb. 5, 2013.
International Search Report; PCT/IB2011/002129; Jan. 26, 2012.

* cited by examiner

*Primary Examiner* — Nyeemah A Grazier
(74) *Attorney, Agent, or Firm* — Westman, Champlin & Koehler, P.A.; Z. Peter Sawicki; Visala Goswitz

(57) ABSTRACT

The synthesis and evaluation of gastroprotective effect of different tryptamine derivatives. Tryptamine derivatives have been synthesized by formation of amide or ester with some known anti oxidant molecules. These derivatives show excellent antioxidant property in vitro. Among all the derivatives the compound SEGA (3a), that was prepared by the combination of serotonin with gallic acid shows the greater antioxidant property than the other synthesized compounds both in vivo and in vitro. SEGA(3a) shows the gastroprotective effect against NSAIDs (indomethacin or diclofenac)-induced gastropathy in dose dependent manner and also accelerates the healing from injury. It prevents the NSAIDs-induced mitochondrial oxidative stress in vivo. This derivative prevents NSAID-induced mitochondrial oxidative stress-mediated apoptosis in vivo by preventing the activation of caspase 9 and caspase-3 and restores NSAIDs-mediated collapse of mitochondroial transmembrane potential and dehydrogenase activity. SEGA (3a) plays an important role as an iron chelator as well as intra mitochondrial ROS scavenger. Thus, SEGA (3a) is a potent antioxidant antiapototic molecule, which efficiently prevents NSAID-induced gastropathy and stress or alcohol-mediated gastric damage.

17 Claims, 15 Drawing Sheets

TRYPTAMINE DERIVATIVES, THEIR PREPARATION AND THEIR USE IN GASTROPATHY

CROSS-REFERENCE TO RELATED APPLICATION

This application is a Section 371 National Stage Application of International Application No. PCT/IB2011/002129, filed Sep. 14, 2009, and published as WO2012/035406 on Mar. 22, 2012, in English, which claims priority of Indian Application 2173/DEL/2010, filed Sep. 14, 2010, the contents of which are hereby incorporated by reference in their entirety.

FIELD OF THE INVENTION

Present invention relates to compounds of general formula 1

General formula 1

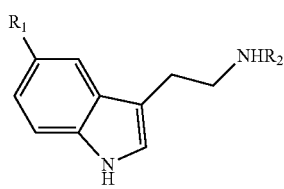

wherein
R$_1$=—OH or —H or —OMe,

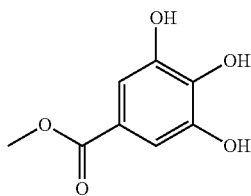

R$_2$=H, —COMe, or

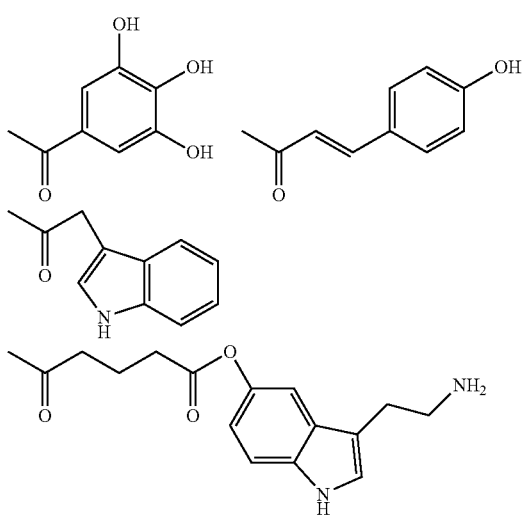

The present invention further relates to tryptamine derivatives of general formula 1 which were synthesized by the formation of amide or ester with some known anti oxidant molecules such as gallic acid, 4-hydroxy cinnamic acid, and indole-3-acetic acid.

Present invention further relates to tryptamine derivatives of general formula 1 useful as antioxidant and antiapoptotic effect to prevent gastropathy/gastric mucosal injury induced by Non-Steroidal Anti-Inflammatory Drugs (NSAIDs), stress and ethanol.

BACKGROUND OF THE INVENTION

Non-Steroidal Anti-Inflammatory Drugs (NSAIDs) are most useful drugs in the world for the treatment of pain, rheumatic disorders, inflammation, and osteo-arthritis (Harth, M; et al. *Br Med J,* 1 (5479), 80-83, 1966).

NSAIDs have antipyretic activity and can be used for the treatment of fever. (Koeberle A; et al. *Curr Med Chem* 16 (32) 2009, 4274-96). So we can not avoid NSAIDs treatment but the major limitation associated with NSAIDs treatment is the development of serious gastropathy or gastric mucosal damage with profuse bleeding and dyspepsia. NSAID-associated upper gastrointestinal adverse events are estimated to result in 103,000 hospitalizations and 16,500 deaths per year in the United States (Green, G. A., *Clin Cornerstone,* 3 (5), 50-60, 2001). NSAIDs are also responsible for Nausea/Vomiting, Diarrhea (Simone Rossi, ed (2006). *Australian medicines handbook* 2006. *Adelaide: Australian Medicines Handbook Pty Ltd*).

Reference may be made to journal "Maity, P; et al. *J Biol Chem,* 283 (21), 14391-14401, 2008", wherein it is well established that the major cause of NSAID-induced gastropathy is the development of oxidative stress in gastric mucosa due to the excess generation of reactive oxygen species (ROS).

It has been documented that ROS induces gastropathy through the induction of both mitochondrial and death-receptor mediated pathway of gastric mucosal cell apoptosis (Maity, P; et al. *J Pineal Res,* 46 (3), 314-323, 2009). In fact, NSAIDs induce mitochondrial pathology, which is associated with increased generation of intra-mitochondrial ROS, such as $O_2.^-$, $H_2O_2$ and .OH leading to oxidative stress. $O_2.^-$ is the most effective to damage mitochondrial aconitase, leading to the release of iron from its iron-sulfur cluster. The released iron, by interacting with intra-mitochondrial $H_2O_2$ forms .OH. Interestingly, intra-mitochondrial .OH generation is crucial for the development of mitochondrial pathology and activation of mitochondrial death pathway by indomethacin (Maity, P.; et al. *J. Biol. Chem.* 284:3058-3068; 2009). Chelation of free iron by desferrioxamin or prevention of the oxidative stress in gastric mucosa can protect gastric mucosal damage (Bandyopadhyay et al. *Life Sci.* 2002 Nov. 1; 71(24): 2845-65). The release and involvement of serotonin (5-hydroxytryptamine) in gastric mucosa (Ogihara, Y; et al. *Jpn J Pharmacol,* 61 (2), 123-131, 1993) is also evident in NSAID-induced gastric mucosal injury. Serotonin (5-hydroxy tryptamine) is a biogenic amine and well known neurotransmitter (Kushnir I H; et al. *Fiziol Zh,* 55 (3), 125-127, 2009).

It is important to mention that serotonin reduces gastric mucosal blood flow (GMBF) by vasoconstriction and thereby causing acute gastric injury (Wong, S. H; et al. *Digestion,* 45 (1), 52-60, 1990, Yoneda, M; et al. *Am J Physiol,* 269 (1 Pt 2), R1-6, 1995) through the generation of ROS by promoting ischemia (Khan, M; et al. *J Pharmacol Exp Ther,* 323 (3), 813-821, 2007). Serotonin adversely affects the defense mechanisms of the gastric mucosa by reducing the secretory function of the mucosal cells and to weaken the epithelial and vascular integrity. Neutrophil activation appears to be responsible for the detrimental effects of 5-HT partly through the elevation in myeloperoxidase (MPO) activity (Ko, J; et al. *Free Radic Biol Med,* 24 (6), 1007-1014, 1998).

It is worth mentioning that serotonin plays an important role in indomethacin, [non-steroidal anti-inflammatory drug (NSAID)], ethanol (Wong, S. H; et al. *Digestion*, 45 (1), 52-60, 1990) and stress-induced gastric ulcer (Debnath, S; et al. *Indian J Exp Biol*, 45 (8), 726-731, 2007). Serotonin can cause oxidative stress through the generation of ROS (Bianchi, P; et al. *FASEB J*, 19 (6), 641-643, 2005). Serotonin is released in response to inflammation (Yoneda, M; et al. *Am J Physiol*, 269 (1 Pt 2), R1-6, 1995) and the increase in mucosal XO activity by serotonin may induce free radical production and possibly modulate the ulcerogenic processes (Ko, J; et al. *Free Radic Biol Med*, 24 (6), 1007-1014, 1998). Serotonin generates ROS by receptor-independent and receptor-dependent mechanisms (Bianchi, P; et al. *FASEB J*, 19 (6), 641-643, 2005). Gastric ulcer or gastropathy is a kind of inflammatory disorder of gastric mucosa (Mierzwa, G; et al. *Med Wieku Rozwoj*, 9 (4), 647-654, 2005).

Thus, it will be of great benefit to synthesize molecule, which will scavenge ROS or chelate free iron and at the same time will prevent the interaction of serotonin with its corresponding receptor to combat NSAID-induced gastropathy or related disorders. Gallic acid (GA), an iron chelator, is a gastroprotective compound and efficiently protects NSAIDs-induced gastric mucosal damage (Pal, C; et al. *Free Radic Biol Med*, 49(2), 258-267; 2010). The mechanistic studies reveal that GA offers gastroprotective effect by preventing the NSAID-induced mitochondrial oxidative stress and apoptosis in gastric mucosal cells and it also prevents the NSAID-induced mitochondrial dysfunction (Pal, C; et al. *Free Radic Biol Med*, 49(2), 258-267; 2010).

Present invention provides different tryptamine (serotonin like molecule) derivatives by formation of amide or ester linkage with GA and some other tryptamine derivatives by replacing GA with some other known antioxidant such as 4-hydroxy cinnamic acid, 3-indole acetic acid. The major disadvantage of serotonin is its toxicity. On the other hand the limitation of GA is its poor bioavailability (Shahrzad, S; et al. *J Nutr*, 131 (4), 1207-1210, 2001). Pharmacokinetics and bioavailability studies indicate that GA is metabolized into 4-O-methylgallic acid very rapidly and the bioavailability in plasma is low. The 38% of the intake of GA were excreted through urine (Shahrzad, S; et al. *J Nutr*, 131 (4), 1207-1210, 2001, Manach, C; et al. *Am J Clin Nutr*, 81 (1 Suppl), 230S-242S, 2005). indole-3-acetic acid and 4-hydroxy cinnamic acid plays an important antioxidant activity by scavenging free radical (Cano, A; et al *Anal Bioanal Chem* (2003) 376: 33-37, Kylli, P; *Anal Bioanal Chem* (2003) 376: 33-37). It has been reported that the serotonin derivative (compound 2b of the present study) can be biosynthesized by the combination of serotonin and 4-hydroxycinnamic acid by serotonin N-hydroxycinnamoyl transferase (SHT) (Kiyoon Kang et al, *Appl Microbiol Biotechnol* (2009) 83:27-34). It was isolated from the seeds of Centaurea montana (Asteraceae), and it shows in vitro cytotoxic activity against the CaCo2 colon cancer cells (Mohammad Shoeb et al, *Tetrahedron* 62 (2006) 11172-11177).

There are some limitations of the existing gastro protective compounds such as proton pump inhibitors (omeprazole, lansoprazole. etc), $H_2$ receptor blockers (ranitidine, cimetidine etc). Although these existing molecules are effective at a very low dose against NSAID-induced gastropathy but it has some adverse effects like diarrhea (Mukherjee, S., J Gastroenterol Hepatol, 18 (5), 602-603, 2003), linear mucosal defects and friable mucosa associated with collagenous colitis, leydig cell tumors, subacute cutaneous lupus erythematosus, myopathy including polymyositis, acute nephritis and anaphylactic reactions (Mukherjee, S., *J Gastroenterol Hepatol*, 18 (5), 602-603, 2003, Clark, D. W; et al. *Fundam Appl Toxicol*, 26 (2), 191-202, 1995). Proton pump inhibitors are reported to be associated with an increased risk of bacterial infection and related diseases (Dial, S; et al. *JAMA*, 292 (16), 1955-1960, 2004).

The synthesized derivatives of the present invention have several advantages. These derivatives can chelate free iron, prevent oxidative stress by scavenging ROS and simultaneously offer antiapoptotic effect in vitro. These derivatives have the ability to prevent the formation of iron-mediated .OH as well as scavenge ROS in vivo. These derivatives can prevent gastric mucosal oxidative stress and gastropathy by preventing ROS-mediated activation of apoptosis in gastric mucosal cells induced by NSAIDs.

OBJECTIVES OF THE INVENTION

The main object of the present invention is to provide compounds of general formula 1.

Another object of the present invention is to provide a new kind of scaffold for the treatment of NSAIDs, ethanol as well as stress-induced gastropathy.

Another object of the present invention is to reduce the toxicity of serotonin by protecting the amine group of the serotonin molecule.

Yet another object of the present invention is to provide a molecule for the treatment of serotonin induced diseases by forming the antagonist of serotonin receptor.

Yet another object of the present invention is to provide an antioxidant molecule in vitro as well as in vivo.

Yet another object of the present invention is to provide an anti apoptotic molecule in vitro as well as in vivo.

Yet another object of the present invention is to provide a molecule that protects mitochondrial oxidative stress as well as mitochondrial dysfunction induced by NSAIDs.

Yet another object of the present invention is to develop mitochondrial iron chelator as well as intra mitochondrial ROS (reactive oxygen species) scavenger.

SUMMARY OF THE INVENTION

Accordingly, present invention provides compounds of general formula 1

General formula 1

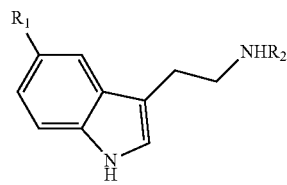

wherein
$R_1$=OH, H, OMe or

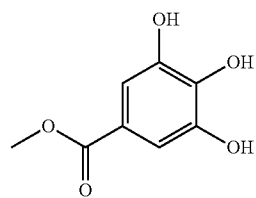

$R_2$=H, —COMe,

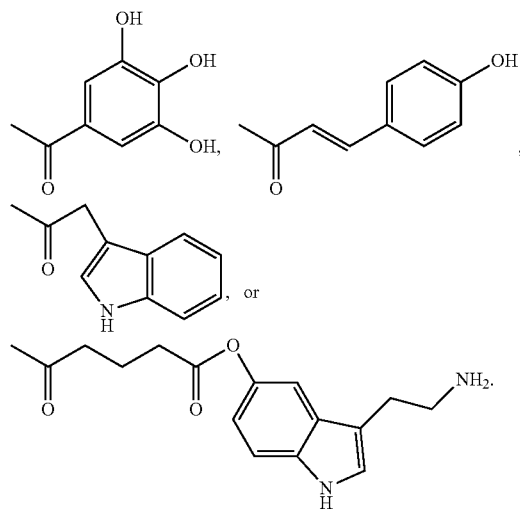

, or

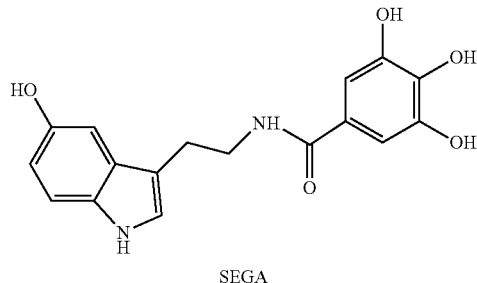

In an embodiment of the present invention, represented compounds comprising:
3,4,5-trihydroxy-N-(2-(5-hydroxy-1H-indol-3-yl)ethyl)benzamide; SEGA (3a);
N-(2-(1H-indol-3-yl)ethyl)-3,4,5-trihydroxybenzamide TRGA (3b);
3,4,5-trihydroxy-N-(2-(5-methoxy-1H-indol-3-yl)ethyl) benzamide MEGA (3c);
(E)-N-(2-(5-hydroxy-1H-indol-3-yl)ethyl)-3-(4-hydroxyphenyl)acrylamide 2b;
(E)-N-(2-(1H-indol-3-yl)ethyl)-3-(4-hydroxyphenyl)acrylamide 2e;
(E)-3-(4-hydroxyphenyl)-N-(2-(5-methoxy-1H-indol-3-yl)ethyl)acrylamide 2h;
N-(2-(5-hydroxy-1H-indol-3-yl)ethyl)-2-(1H-indol-3-yl)acetamide 2c;
N-(2-(1H-indol-3-yl)ethyl)-2-(1H-indol-3-yl)acetamide 2f;
2-(1H-indol-3-yl)-N-(2-(5-methoxy-1H-indol-3-yl)ethyl) acetamide; 2i;
3-(2-aminoethyl)-1H-indol-5-yl 3,4,5-trihydroxybenzoate GA SA (4d);
3-(2-aminoethyl)-1H-indol-5-yl 5-(2-(5-hydroxy-1H-indol-3-yl)ethylamino)-5-oxopentanoate 6c;
N-(2-(5-hydroxy-1H-indol-3-yl)ethyl)acetamide 5a.

In another embodiment of the present invention, the structural formulae of the representative compounds are:

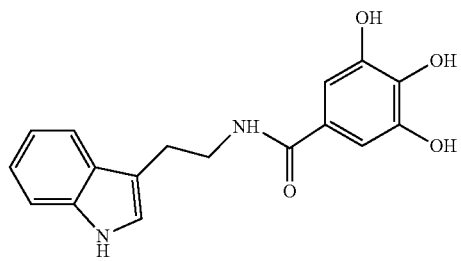

TRGA (3b)

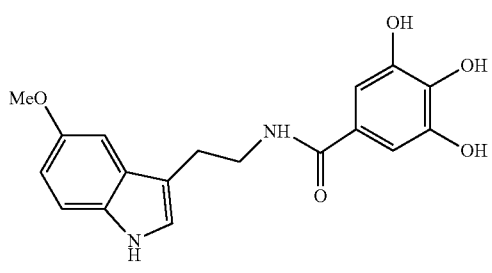

MEGA (3c)

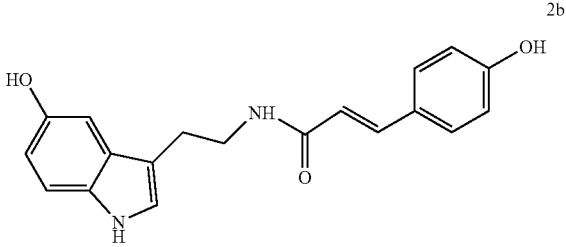

2b

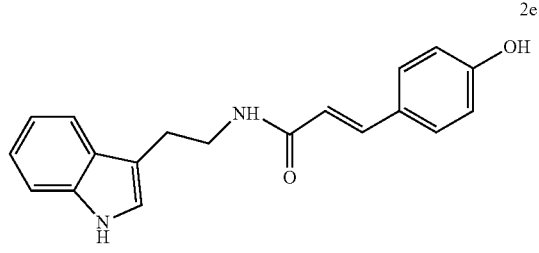

2e

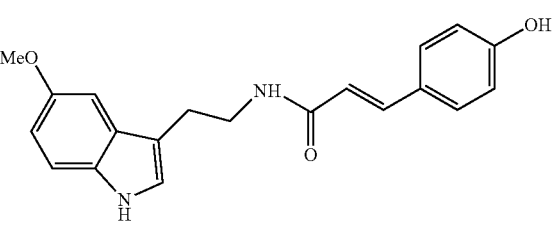

2h

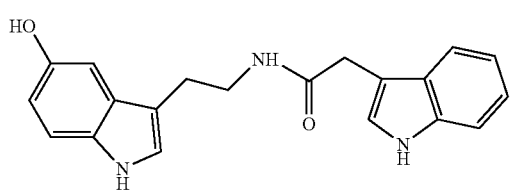

2c

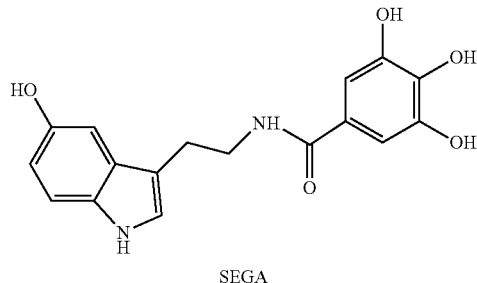

SEGA (3a)

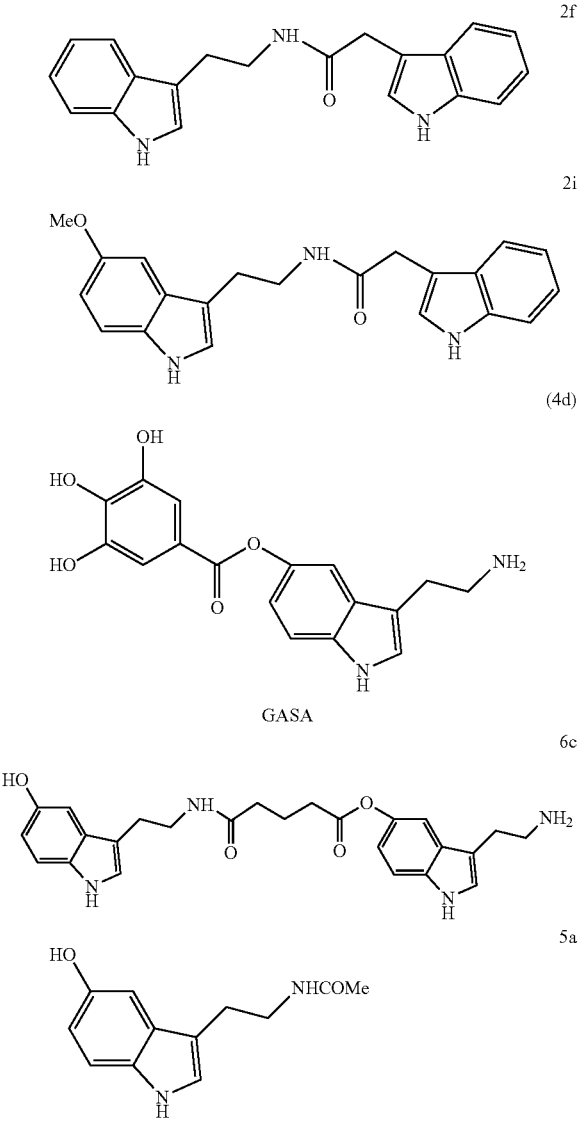

In yet another embodiment of the present invention, said compounds are useful for the treatment of gastropathy.

In yet another embodiment of the present invention, said compounds exhibiting antioxidant property in vitro.

In yet another embodiment of the present invention, ferric reducing antioxidant power (FRAP) value at 6 min, 65 min and absorbance change value in 2,2-Diphenyl-1-Picrylhydrazyl (DPPH) assay are in the range of 1.65±0.06 to 39.51±2.7, 1.83±0.29 to 60.61±7.3 and 0.107±0.02 to 0.449±0.08 respectively.

In yet another embodiment of the present invention, compounds of formula SEGA, GASA, TRGA and MEGA exhibiting ulcer index value in the range of 30±3 to 61±3.

In yet another embodiment of the present invention, pharmaceutical composition comprising at least one compound of general formula 1 with pharmaceutically acceptable carrier.

In yet another embodiment of the present invention, a method for treating gastropathy in an animal comprising administrating the effective amount of at least one compound of general formula 1.

In yet another embodiment of the present invention, said gastropathy is due to non-steroidal anti-inflammatory drugs (NSAIDs), ethanol and cold-immobilized stress through the development of mitochondrial oxidative stress and subsequent induction of gastric mucosal cell apoptosis.

In yet another embodiment of the present invention, effective amount of compound of general formula 1 is in the range of 1 mg kg$^{-1}$ to 50 mg kg$^{-1}$.

In yet another embodiment of the present invention, compound of general formula 1 is administered intraperitoneally.

In yet another embodiment of the present invention, $ED_{50}$ value for compound SEGA (3a) is in the range of 6 to 8 mg kg$^{-1}$.

In yet another embodiment of the present invention, compound of formula SEGA(3a) is a non toxic molecule as established by 3[4,5-dimethylthiazol-2-yl]-2,5-diphenyltetrazolium bromide (MTT) reduction assay.

In yet another embodiment of the present invention, a method for preventing damage in-vitro in cultured gastric mucosa cell comprising administrating the effective amount of at least one compound of general formula 1.

In yet another embodiment of the present invention, A process for the preparation of compounds of formula SEGA (3a), 2b, 2c, TRGA (3b), 2e, 2f, MEGA (3c), 2h, 2i, 4d as claimed in claim 2 comprising the steps of:
  i. condensing tryptamine derivatives and substituted acid in the ratio ranging between 1:1.2 to 1:2 using 1-Ethyl-3-(3-dimethyllaminopropyl)carbodiimide hydrochloride (EDC hydrochloride) followed by isolating by elution with 2 to 3% methanol in chloroform to obtain compound of formula 2a-I, 4b and 6b;
  ii. hydrogenating compound of formula 2a, 2d and 2d to obtain compound of formula 3a, 3b, 3c and 4c;
  iii. mixing 6b as obtained in step (i) or 4c as obtained in step (ii) in 10 to 20% $CH_2Cl_2$ and formic acid at temperature in the range of 0 to 1° C. followed by stiffing at temperature in the range of 25 to 27° C. for period in the range of 50 80 minutes to obtain 6c and 4d respectively.

In yet another embodiment of the present invention, tryptamine derivatives are selected from the group consisting of serotonin hydrochloride (5-hydroxy tryptamine hydrochloride), tryptamine hydrochloride, 5-methoxy tryptamine, tert butyl 2-(5-hydroxy-1H-indol-3-yl)ethyl carbamate.

In yet another embodiment of the present invention, substituted acids are selected from the group consisting of 3,4,5-tris(benzyloxy)benzoic acid, 4-hydroxy cinnamic acid, indole-3-acetic acid, serotonin hydrochloride (5-hydroxy tryptamine hydrochloride).

In yet another embodiment of the present invention, compound SEGA (3a) reduces the NSAID-induced gastric mucosal apoptosis by performing the Terminal deoxynucleotidyl Transferased UTP Nick End Labeling (TUNEL) assay as well as by inhibiting NSAID-induced caspase-3 activity in vivo.

In yet another embodiment of the present invention, compound SEGA (3a) protects the mitochondrial pathway of apoptosis by inhibiting the NSAID-induced caspase-9 activity.

In yet another embodiment of the present invention, compound SEGA (3a) prevents NSAIDs-induced formation of mitochondrial protein carbonyl.

In yet another embodiment of the present invention, compound SEGA (3a) protects the NSAIDs-induced mitochondrial lipid peroxidation.

In yet another embodiment of the present invention, compound SEGA (3a) prevents the NSAIDs-induced depletion of mitochondrial total thiol.

In yet another embodiment of the present invention, said compound SEGA (3a) scavenges the free iron in the cultured cells to protects the intracellular reactive oxygen species (ROS) generation.

In yet another embodiment of the present invention, said compound SEGA (3a) prevents NSAIDs-induced inhibition of mitochondrial dehydrogenase activity.

DETAILED DESCRIPTION OF THE INVENTION

In the present invention, tryptamine derivatives SEGA (3a), TRGA (3b), MEGA (3c), GASA (4d), 2b, 2c, 2e, 2f, 2h, 2i, 5c, and 6c were synthesized by condensation of serotonin, tryptamine, 5-methoxytryptamine with some known antioxidant such as gallic acid, 4-hydroxy cinnamic acid, indole-3-acetic acid etc. Among all these derivatives the compound SEGA (3a), prepared by combining serotonin and gallic acid, shows the greater anti-oxidant property in vitro than the other derivatives.

Figure 1:
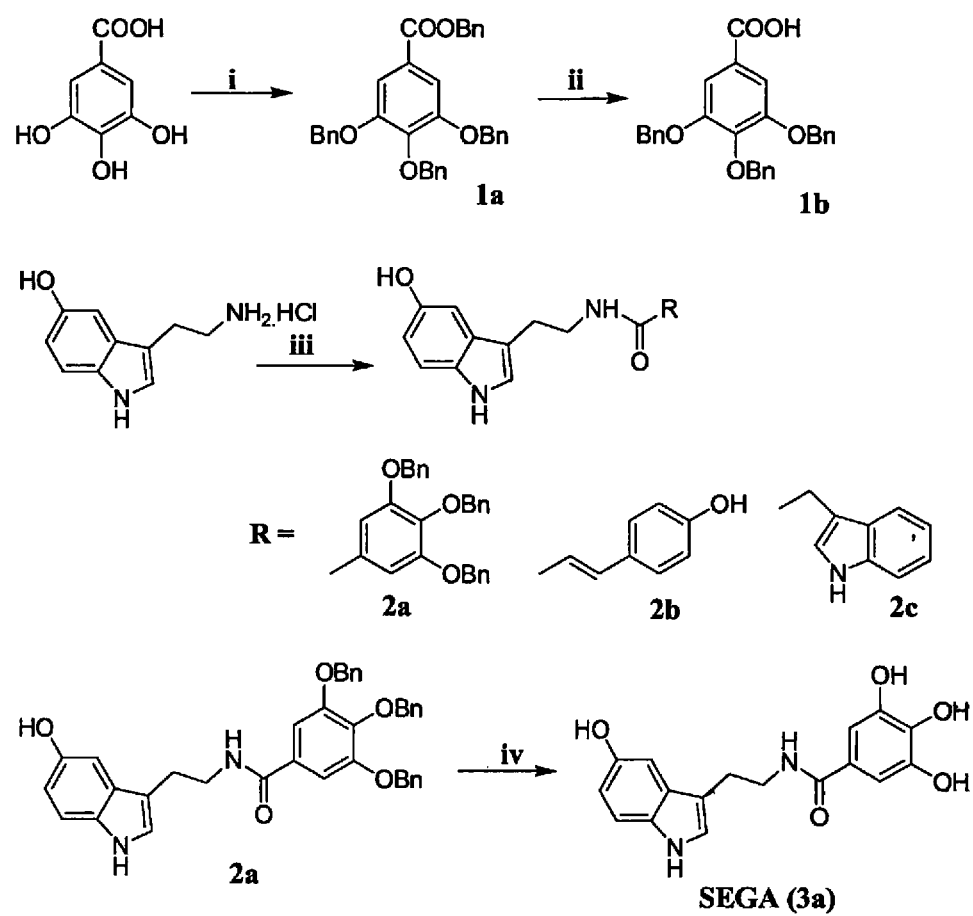
FIG. 1 represents synthetic scheme of SEGA (3a), 2b, 2c wherein Reagents and condition are (i) Benzyl chloride, $K_2CO_3$, $Bu_4N^+I^-$, acetone reflux 4 h, 80%; (ii) 20% KOH, ethanol, reflux 3 h, 84%; (iii) Serotonin hydrochloride, RCOOH, EDC-HCl, $Et_3N$, DMF, overnight rt; (iv) 10% Pd—C, methanol rt (room temperature, 27° C.), 2 h.
Figure 2:
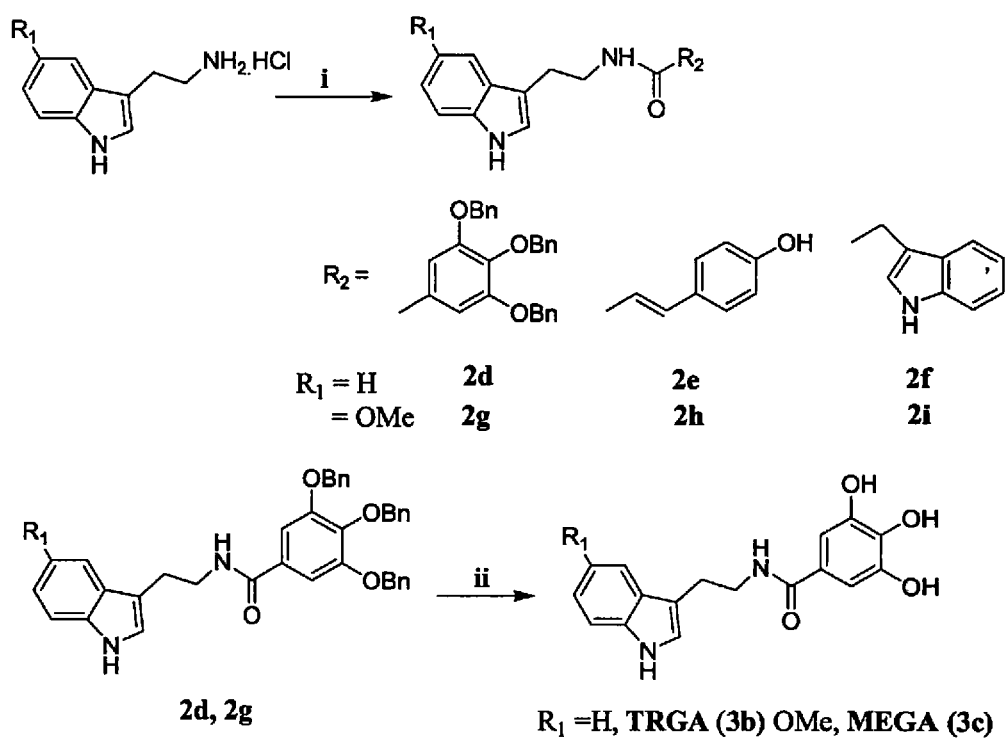
FIG. 2 represents synthetic scheme of TRGA (3b), MEGA (3c), 2e, 2f, 2h, and 2i wherein Reagents and condition are (i) $R_1NH_2$, $R_2COOH$, EDC-HCl, $Et_3N$, DMF, 12 h, rt (room temperature, 27° C.) (iv) 10% Pd—C, methanol rt (room temperature, 27° C.), 30 min.
Figure 3:
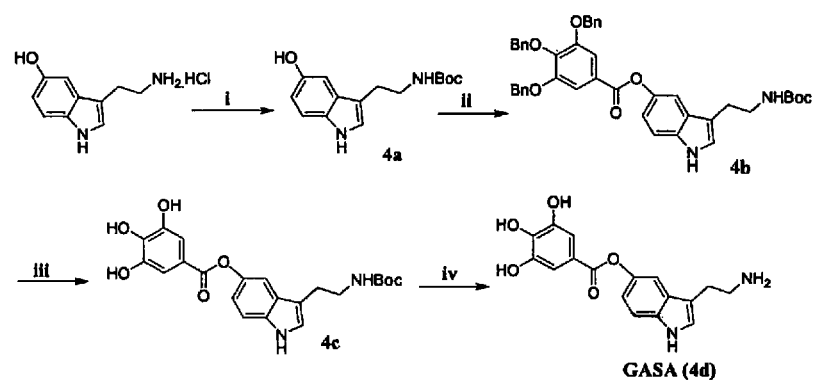
FIG. 3 represents synthetic scheme of GASA (4d) wherein Reagents and condition are (i) $NaHCO_3$, NaCl, $H_2O$, $(BOC)_2O$, $CHCl_3$, reflux 3 h, 95%; (ii) 1b, EDC-HCl, DMAP, DMF, rt (room temperature, 27° C.), 12 h (iii) 10% Pd—C, methanol rt, 2 h. (iv) $CH_2Cl_2$, 96% HCOOH, 30% aqueous $NH_3$, rt (room temperature, 27° C.), 3 h, 81%.
Figure 4:
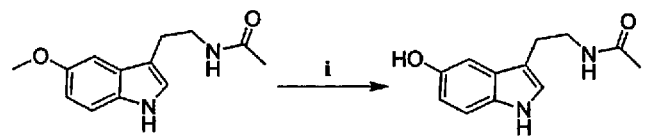
FIG. 4 represents synthetic scheme of 5c wherein Reagents and condition are (i) $BBr_3$, DCM, −78° C., rt (room temperature, 27° C.) overnight, 45%.
Figure 5:
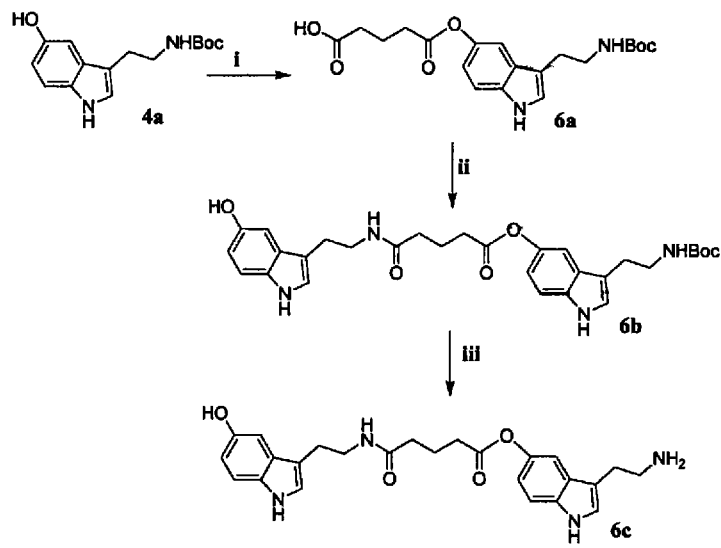
FIG. 5 represents synthetic scheme of 6c wherein Reagents and condition are (i) Glutaric anhydride, DMAP, $Et_3N$, THF, reflux 4 h, 74%; (ii) Serotonin hydrochloride, EDC-HCl, $Et_3N$, DMF, (room temperature, 27° C.), 12 h, 56%; (iii) $CH_2Cl_2$, 96% HCOOH, 30% aqueous $NH_3$, rt 3 h, 81%.

The primary amine group of serotonin is derivatized into various amide derivatives such as N-gallyl (SEGA) 3a, N-cinnamyl 2b and N-indole acetyl 2c respectively. These derivatives were synthesized by condensation of serotonin with benzylated gallic acid, 4-hydroxycinnamic acid and indol-3-acetic acid respectively in presence of 1-Ethyl-3-(3-dimethylaminopropyl)carbodiimide (EDC.HCl) and Hydroxybenzotriazole (HOBt) in N,N-dimethyl formamide (DMF), followed by hydrogenolysis (for 3a) in presence of 10% Pd—C/H$_2$ as outlined in the (FIG. 1). For the gallic acid derivatives with different amines, gallic acid was treated with benzyl chloride in presence of potassium carbonate and catalytic tetra n-butyl ammonium iodide to give benzyl 3,4,5-tris (benzyloxy)benzoate (1a), which upon hydrolysis with ethanolic 20% KOH solution under reflux provided 3,4,5-tris (benzyloxy)benzoic acid, (1b) (FIG. 1). To assess the importance of the free hydroxyl functional group of serotonin at 5-position of indole nucleus, further 5-deoxy derivative TRGA (3b) and 5-methoxy derivative 3c using tryptamine hydrochloride and 5-methoxy tryptamine respectively have synthesized. Condensation of these amines with 4-hydroxy cinnamic acid, indole-3-acetic acid, 4,5-tris(benzyloxy)benzoic acid (1b), using the same procedure as described before, furnished amide derivatives (FIG. 2) 2e, 2f, 2h, 2i, 3b, and 3c respectively in good yields. In order to understand the effect of gallic acid as substituent in serotonin-gallic acid conjugate (whether gallic acid is attached to primary amine group of serotonin as N-gallyl amide orelse it is attached to free hydroxyl functionality of serotoin as o-gally ester) and in addition to see the effect of free amine group in serotonin-gallic acid conjugate, further o-gallyl ester GASA (4d) (FIG. 3) have synthesized. For the preparation of o-gallyl ester (4d), the primary amine group was protected with Boc using di-tert-butyloxycarbonyl anhydride to give tert-butyl 2-(5-hydroxy-1H-indol-3-yl)ethylcarbamate (4a) (Breitinger, H. G; et al. Biochemistry, 39 (18), 5500-5508, 2000). Condensation of Boc-Protected serotonin 4a with 3,4,5-tris(benzyloxy)benzoic acid (1b), yielded the ester 4b, which upon hydrogenolysis with 10% Pd—C/H$_2$ followed by deprotection of the Boc group in presence of 96% formic acid provided the required compound, GASA (4d) (FIG. 3). To see the importance of free methoxy functionality of melatonin at 5-position of indole nucleus, 5-hydroxy derivative 5c have also synthesized, by treating melatonin with BBr$_3$ at $-78°$ C. in 45% yield as shown in (FIG. 3) (Srivastava, V; et al. Bioorg Med Chem, 15 (1), 518-525, 2007). To the end, dimeric serotonin derivative 6c was synthesized for structure-activity relationship study (SAR) starting from serotonin as shown in FIG. 4. Accordingly, Boc protected serotonin 4a was converted into the carboxylic acid derivative 6a, by treating with glutaric anhydride in presence of trimethyl amine and N,N dimethylamino pyridine (DMAP) (Shi, W; et al. Org Lett, 9 (26), 5461-5464, 2007). Condensation of 6a with another serotonin molecule in presence of EDC afforded the compound 6b, which on subsequent treatment with 96% formic acid provided the required serotonin dimer 6c (FIG. 4).

All these derivatives play an important antioxidant activity in vitro by reducing Fe (III) in to Fe (II) in the ferric reducing antioxidant power assay (FRAP assay) and also scavenging DPPH free radicals in DPPH assay. These experiments were performed in presence of some known anti oxidant available in the markets. SEGA (3a) shows the greater antioxidant activity than the known anti oxidant.

These derivatives protect the gastric mucosa from NSAIDs (indomethacin, diclofenac)-induced gastric mucosal damage in a dose dependent manner. These derivatives also protect gastric mucosa against stress and ethanol-induced injury SEGA (3a) shows the gastro protective effect in NSAIDs (indomethacin, diclofenac)-induced gastropathy in dose dependent manner, it also prevent the ethanol, stress-induced gastropathy.

SEGA (3a) protects NSAIDs-induced mitochondrial oxidative stress by preventing NSAIDs-mediated mitochondrial protein carbonyl formation, peroxidation of mitochondrial protein, and depletion of total thiol content in mitochondria.

SEGA (3a) protects indomethacin-induced apoptosis in gastric mucosa in vivo as evident from the TUNEL assay and by preventing the indomethacin-induced caspase-3 activation. It also protects the apoptosis in in vitro cultured gastric mucosa by as manifested by the TUNEL assay. SEGA (3a) protects the mitochondrial path way of apoptosis by preventing the indomethacin-induced caspase-9 activation.

SEGA (3a) prevents NSAIDs-induced mitochondrial dysfunction, restores the NSAIDs-induced fall off mitochondrial membrane potential, checks the indomethacin-induced reduction in mitochondrial dehydrogenase activity and scavenges intra mitochondrial superoxide. It plays an important role as a mitochondrial iron chelator as well as intra mitochondrial ROS i.e. superoxide scavenger.

TABLE 1

FRAP value of different test compounds at 6 min and 65 min

| Compounds | FRAP Value$_{6\,min}$ (µM) M ± SD | FRAP Value$_{65\,min}$ (µM) M ± SD |
|---|---|---|
| 3a | 39.51 ± 2.7 | 60.61 ± 7.3 |
| 3b | 14.32 ± 0.36 | 19.65 ± 2.1 |
| 3c | 15.32 ± 0.46 | 21.96 ± 2.6 |
| 2e | 2.45 ± 0.19 | 5.60 ± 1.02 |
| 2b | 3.09 ± 0.13 | 7.44 ± 1.47 |
| 2h | 1.87 ± 0.13 | 2.93 ± 1.43 |
| 2f | 2.44 ± 0.24 | 3.33 ± 0.49 |
| 2c | 2.48 ± 0.10 | 3.57 ± 0.41 |
| 2i | 1.94 ± 0.04 | 2.5 ± 0.34 |
| 4d | 24.02 ± 1.98 | 35.40 ± 3.25 |
| 6c | 17.51 ± 0.38 | 29.78 ± 3.87 |
| Gallic acid | 33.90 ± 4.92 | 46.59 ± 8.41 |
| Melatonin | 1.65 ± 0.06 | 1.83 ± 0.29 |
| Serotonin | 21.61 ± 3.65 | 35.48 ± 6.55 |
| Quercetin | 28.11 ± 1.00 | 48.55 ± 4.85 |
| Ascorbic acid | 15.46 ± 0.07 | 15.89 ± 2.24 |

Values are the means ± SEM of at least three experiments.

TABLE 2

Absorbance change of different test compounds at 30 min in DPPH scavenging assay

| Compounds (100 µM) | Absorbance change (ΔA) at 30 min |
|---|---|
| 3a | 0.45 ± 0.08 |
| 3b | 0.31 ± 0.06 |
| 3c | 0.35 ± 0.08 |
| 2e | 0.11 ± 0.02 |
| 2b | 0.12 ± 0.01 |
| 2h | 0.11 ± 0.03 |
| 2f | 0.13 ± 0.03 |
| 2c | 0.14 ± 0.04 |
| 2i | 0.12 ± 0.02 |
| 4d | 0.38 ± 0.07 |
| 6c | 0.19 ± 0.03 |

TABLE 3

Absorbance change of different test compounds at different concentration in DPPH scavenging assay

| Compounds | Concentration(µM) | Absorbance change (ΔA) at 30 min |
|---|---|---|
| SEGA (3a) | 10 | 0.27 ± 0.03 |
|  | 30 | 0.34 ± 0.05 |
|  | 50 | 0.37 ± 0.07 |
|  | 80 | 0.42 ± 0.07 |
|  | 100 | 0.45 ± 0.08 |
| GASA (4d) | 10 | 0.18 ± 0.01 |
|  | 30 | 0.27 ± 0.03 |
|  | 50 | 0.31 ± 0.05 |
|  | 80 | 0.33 ± 0.05 |
|  | 100 | 0.38 ± 0.07 |

TABLE 3-continued

Absorbance change of different test compounds at different concentration in DPPH scavenging assay

| Compounds | Concentration(μM) | Absorbance change (ΔA) at 30 min |
|---|---|---|
| MEGA (3c) | 10 | 0.18 ± 0.02 |
|  | 30 | 0.24 ± 0.03 |
|  | 50 | 0.28 ± 0.05 |
|  | 80 | 0.31 ± 0.07 |
|  | 100 | 0.35 ± 0.08 |
| TRGA (3b) | 10 | 0.16 ± 0.02 |
|  | 30 | 0.21 ± 0.05 |
|  | 50 | 0.23 ± 0.04 |
|  | 80 | 0.28 ± 0.03 |
|  | 100 | 0.31 ± 0.06 |

TABLE 4

Effect of other derivatives on NSAID-induced gastric mucosal damage in animal models

| Compounds | Gastric mucosal damage (ulcer index) |
|---|---|
| Indomethacin (48 mg kg$^{-1}$) | 61 ± 3 |
| SEGA (6.9 mg kg$^{-1}$) | 30 ± 3 |
| GASA (6.9 mg kg$^{-1}$) | 41 ± 2.5 |
| TRGA (6.9 mg kg$^{-1}$) | 42 ± 2 |
| MEGA (6.9 mg kg$^{-1}$) | 39 ± 2 |

Values are the means ± SEM of at least six experiments.

Biological Effects

Figure 6:
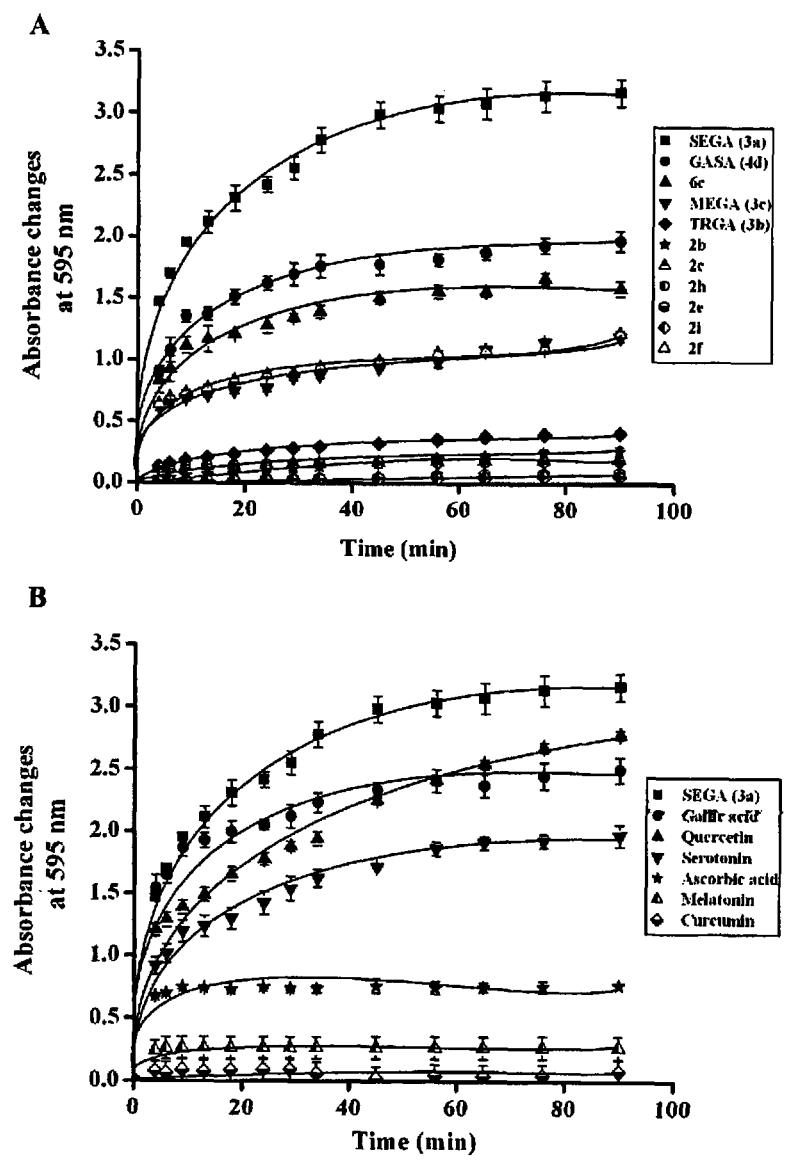
FIG. 6 represents tryptamine derivatives shows antioxidant property in vitro. (A) Absorbance changes at 595 nm were monitored at different time intervals in presence of different tryptamine derivatives in the ferric reducing antioxidant power (FRAP) assay. The values are the mean±SEM of triplicate sets. (B) Comparative analysis of antioxidant activity of tryptamine derivatives with some known antioxidant at different time intervals. The values are the mean±SEM of triplicate sets.
Figure 7:
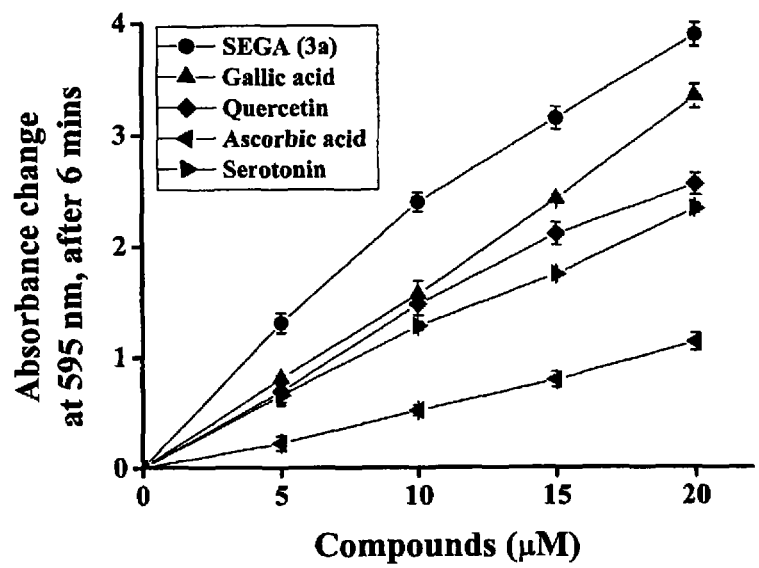
FIG. 7 represents comparative analysis of antioxidant activity of SEGA (3a) with some known antioxidant at different concentrations in FRAP assay.
Figure 8:
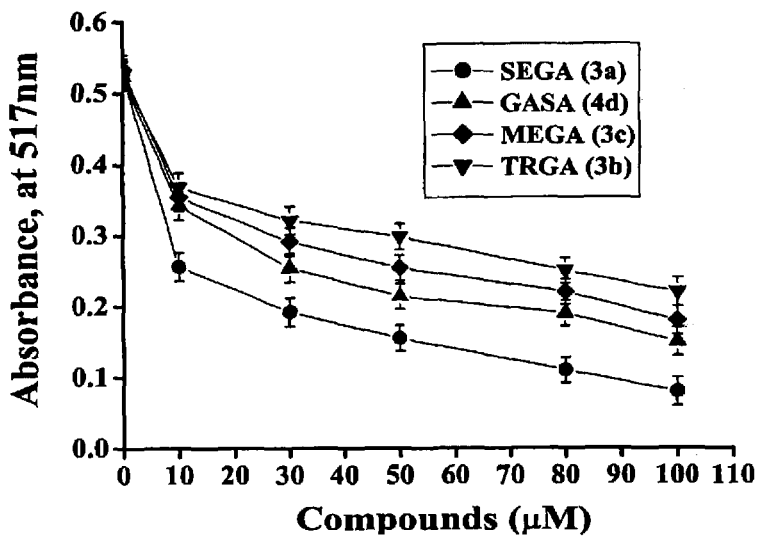
FIG. 8 represents 2,2-Diphenyl-1-Picrylhydrazyl (DPPH) free radical scavenging activity of different tryptamine derivatives at different concentrations.

The antioxidant property of different tryptamine derivatives were assessed and compared with the known antioxidants for potency. A range of different synthesized compounds and known anti oxidants, quercetin, ascorbic acid and gallic acid were analyzed by the FRAP assay. The FRAP assay is based on the measurement of the ability of the substance to reduce $Fe^{3+}$ to $Fe^{2+}$, greater the reducing ability greater the anti oxidant property. Antioxidants reduce $Fe^{3+}$-TPTZ in to blue colored $Fe^{2+}$-TPTZ complex, which results in an increase in the absorbance at 595 nm giving a FRAP value. Higher FRAP value indicates that greater reducing (i.e. antioxidant property) ability of the compound. Absorbance changes at different time intervals (FIG. 6) as well as at different concentrations (FIG. 7) at time 6 min in the presence of different compounds at 595 nm were measured. FRAP values at 6 min and 65 min were calculated from different tryptamine derivatives and some known antioxidant (Table 1). Results clearly indicate that serotonin-gallic acid conjugate SEGA (3a) shows greater reducing ability ($Fe^{3+}$ to $Fe^{2+}$) compare to other tryptamine derivative as well as known antioxidant (gallic acid, quercetin, and ascorbic acid). Serotonin shows very little antioxidant property and the antioxidant property is not increased even after dimerisation thus indicating very insignificant native anti oxidant property of serotonin Anti oxidant property of these synthesized derivatives were further verified by the DPPH assay. DPPH assay based on the DPPH free radicals scavenging power of the antioxidant molecules. Higher the scavenging power higher will be the antioxidant property. The results indicate that among all the derivatives SEGA (3a) shows the higher scavenging power (FIG. 8) (Table 2 and table 3). This assay was performed in presence of some known antioxidants such as ascorbic acid, quercetin and gallic acid. The results indicate that SEGA (3a) shows almost equal antioxidant power to these known antioxidants (data not shown).

Figure 9:
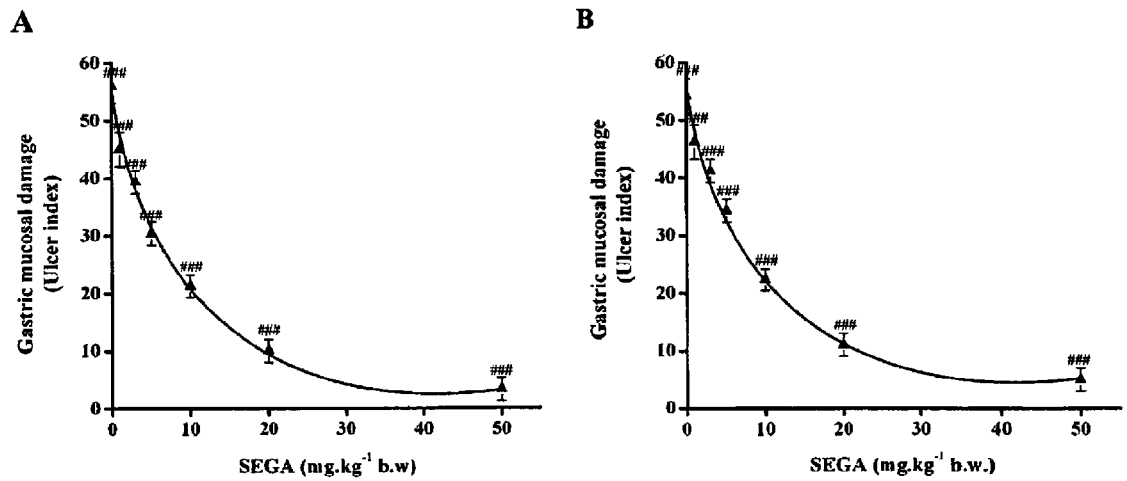
FIG. 9 (A) represents protection of indomethacin-induced gastric mucosal damage by SEGA (3a) at different doses as measured by ulcer index. (B) SEGA (3a) protects diclofinac-induced gastropathy as measured by ulcer index as described under "Materials and methods". Data were presented as mean±SEM. ($^{\#\#\#}$=p<0.001 vs. indomethacin or diclofenac, n=6).
Figure 10:
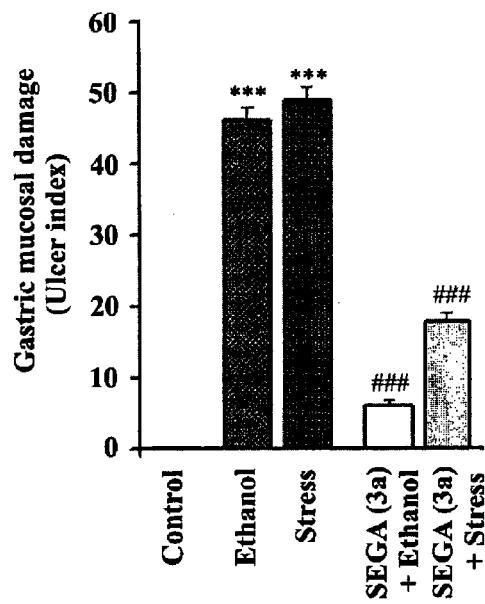
FIG. 10 represents effect of SEGA (3a) on ethanol, stress-induced gastric mucosal damage in animal (rat) models. (***=p<0.001 vs control, $^{\#\#\#}$=p<0.001 vs. ethanol or stress, n=5).
Figure 11:
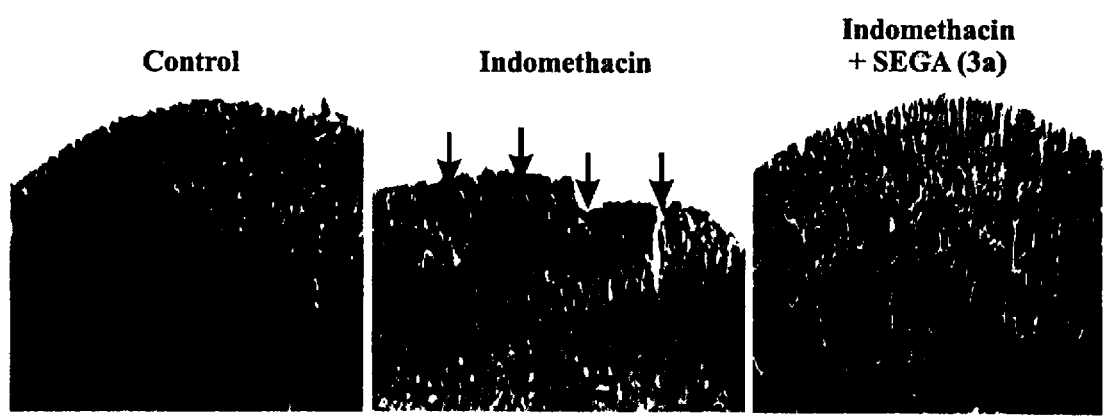
FIG. 11 represents haematoxylin-eosin staining of gastric mucosal sections from control, indomethacin-treated and SEGA (3a) pretreated indomethacin-treated rats.
Figure 12:
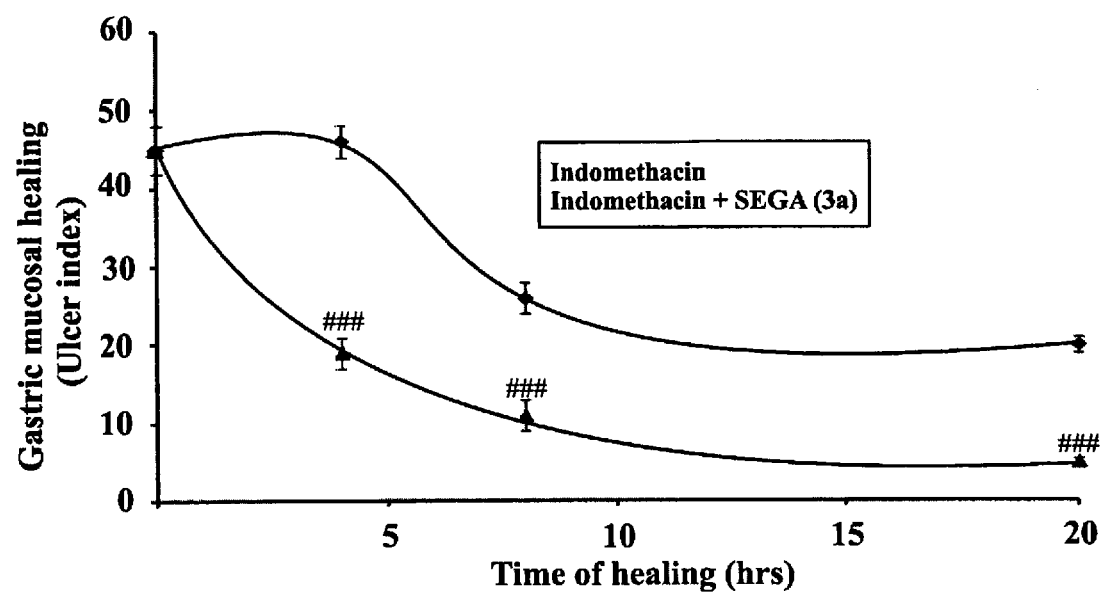
FIG. 12 represents SEGA (3a) accelerates healing of indomethacin-induced gastric mucosal injury as measured by ulcer index as. Data were presented as mean±SEM. ($^{\#\#\#}$=p<0.001 vs. indomethacin, n=4).

SEGA (3a) (dissolved in 0.05 N NaOH) dose dependently ($ED_{50}$ 6.9 mg kg$^{-1}$) prevents indomethacin-induced gastric mucosal damage. In case of indomethacin-induced gastric mucosal injury, SEGA (3a) offers 94%, 82%, 62%, 45%, 28%, and 17% and in case of diclofenac induced ulcer it offers 82%, 72%, 57%, 42%, 25%, and 22% protection at the dose of 50, 20, 10, 5, 3, and 1 mg kg$^{-1}$ respectively (FIG. 9). SEGA (3a) not only show the gastroprotective effect on NSAIDs-induced gastropathy it also protects the gastric mucosa in the ethanol, stress induced gastropathy (FIG. 10). To see the changes in the microscopic anatomy of the gastric mucosal tissue in control, indomethacin treated and SEGA (3a) pre-treated indomethacin-treated sample we did the histological studies (FIG. 11). This further demonstrated that SEGA (3a) could protect gastric mucosa from the indomethacin induced increased gastric mucosal cell damage and cell shedding leading to the development of damage in the superficial mucosa. To see the effect of other tryptamine derivatives over the indomethacin-induced gastropathy, all the derivatives of tryptamine TRGA (3b), MEGA (3c), GASA (4d) (dissolved in 0.05 N NaOH) were administered intraperitoneally at $ED_{50}$ dose of SEGA (3a) i.e. 6.9 mg kg$^{-1}$. The results indicate that these derivatives have the lesser gastroprotective effect than the SEGA (3a) (Table. 4). To observe the effect of only serotonin on gastropathy we synthesized serotonin dimmer (6c), when this compound was injected all the rats were found dead within 20 mins. From this experiment it is clear that serotonin is a toxic molecule. To cross check this result we administered serotonin i.p. at the dose 50 mg kg$^{-1}$, and 25 mg kg$^{-1}$ and again all the rats were found to be dead. Thus we can conclude that serotonin is a toxic molecule on the other hand serotonin derived compound SEGA (3a) is a nontoxic molecule. Thus from this experiment we can conclude that by blocking the amine group of serotonin with gallic acid we detoxify the serotonin molecule. It also rescues the NSAIDs-induced already damaged gastric mucosa, i.e. it accelerates the healing process (FIG. 12).

Figure 13:
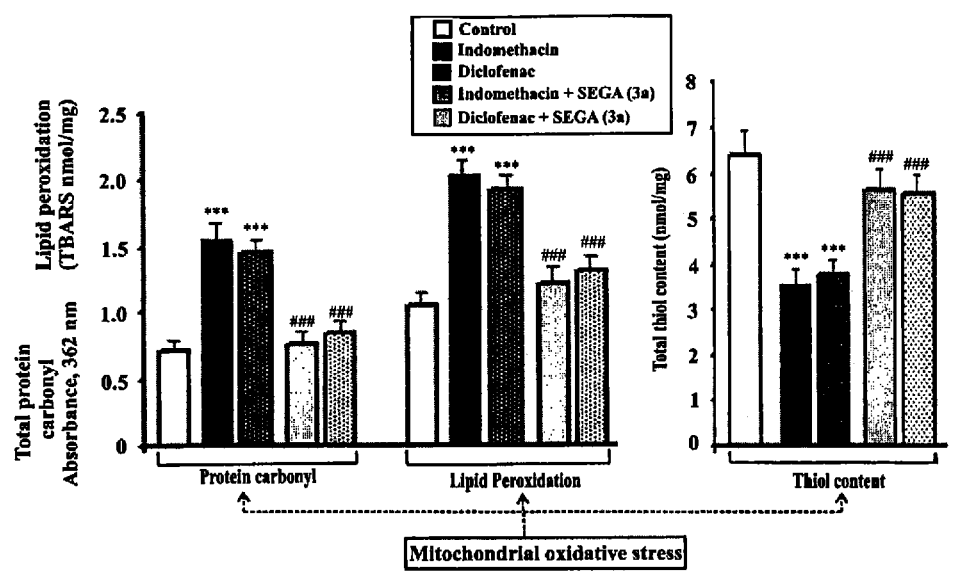
FIG. 13 represents SEGA (3a) protects the Non-steroidal anti-inflammatory drugs (NSAIDs)-induced mitochondrial oxidative stress in vivo. SEGA (3a) protects the indomethacin, diclofenac-induced formation of protein carbonyl in mitochondria, peroxidation of mitochondrial lipid and protects the indomethacin, diclofenac-induced decrement of thiol content in mitochondria. Data were presented as mean±SEM (***=p<0.001 vs control, $^{\#\#\#}$=p<0.001 vs. indomethacin, n=5).
Figure 14:
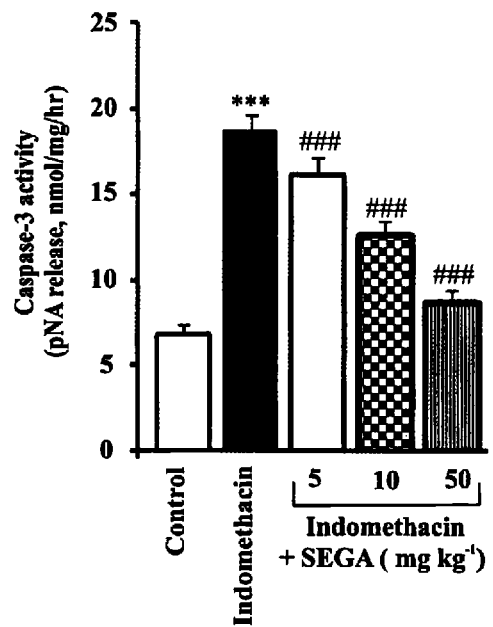
FIG. 14 represents SEGA (3a) protects indomethacin-induced apoptosis in-vivo. (A) SEGA prevents the inodomethacin induced caspae-3 activity in dose dependent manner. Data were presented as mean±SEM, (***=p<0.001 vs control, $^{\#\#\#}$=p<0.001 vs. indomethacin, n=6). (B) Terminal deoxynucleotidyl transferase dUTP nick end labeling (TUNEL) assay (deep brown staining suggests apoptotic DNA fragmentation, indicated by arrows) shows that indomethacin triggers apoptosis of gastric mucosal cells and SEGA (3a) blocks indomethacin-induced gastric mucosal apoptosis.
Figure 14:
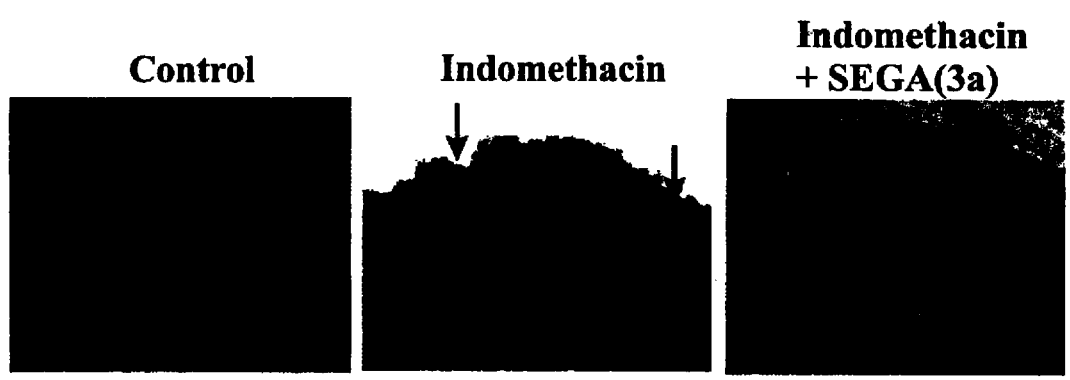
Figure 15:
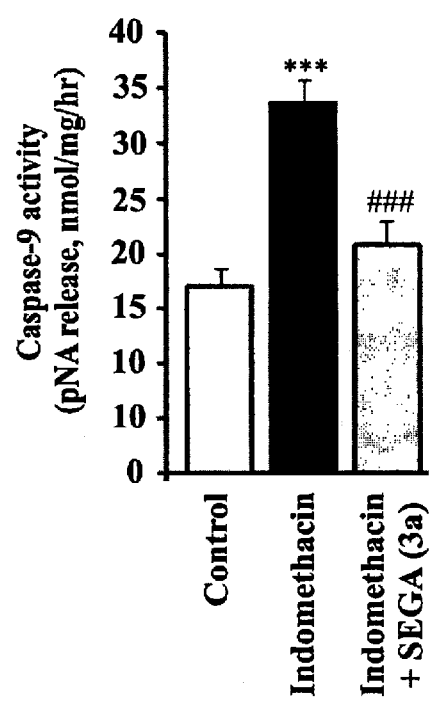
FIG. 15 represents SEGA (3a) protects indomethacin-induced mitochondrial path way of apoptosis in vivo. SEGA prevents the inodomethacin induced caspae-9 activity. Data were presented as mean±SEM, (***=p<0.001 vs control, $^{\#\#\#}$=p<0.001 vs. indomethacin, n=6).
Figure 16:
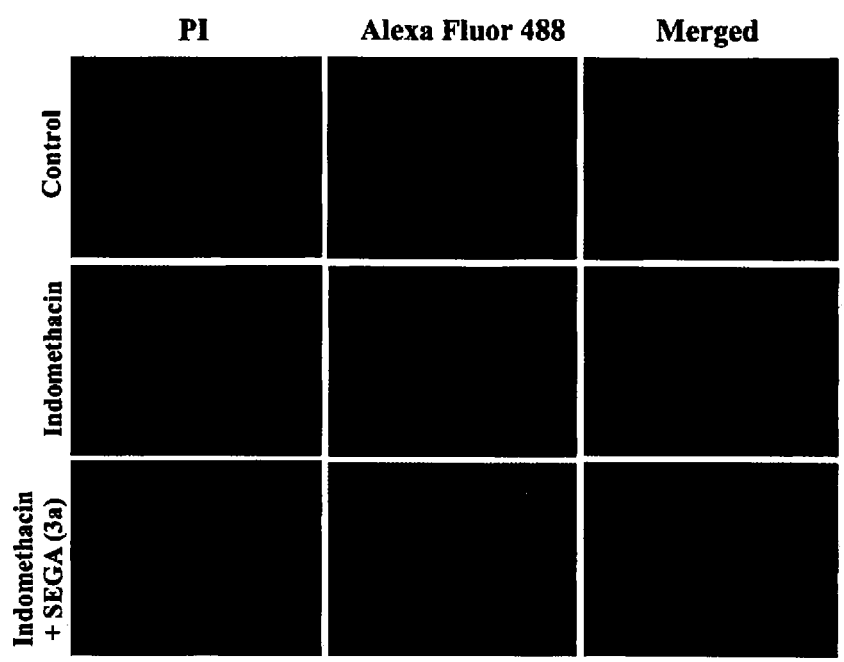
FIG. 16 represents SEGA (3a) protects indomethacin-induced gastric mucosal cell apoptosis in vitro. TUNEL assay shows GA inhibits apoptosis in primary cultured gastric epithelial cells, The first column shows nuclei stained with propidium iodide (PI), the second column shows apoptotic DNA fragmentation stained with Alexa Flour 488 and third column shows the merged pictures of first (PI) and second (Alexa Flour 488) column.

Compound SEGA (3a) significantly protected NSAIDs (indomethcin, diclofenac)-induced mitochondrial oxidative stress; it protects oxidation of mitochondrial protein (protein carbonyl formation), depletion of mitochondrial thiol, and peroxidation of mitochondrial lipid. The results showed that increased formation of protein carbonyl, peroxidation of mitochondrial lipid and depletion of the mitochondrial thiol at the gastric mucosa, but pretreatment with the compound SEGA (3a) prevented NSAIDs (indomethcin, diclofenac)-induced mitochondrial oxidative stress (FIG. 13) Thus, from this experiment we can say that compound SEGA plays an important antioxidant role in vivo SEGA (3a) prevents oxidative stress-induced gastric mucosal apoptosis during ulceration. Indomethacin induces gastric mucosal apoptosis through the generation of ROS and subsequent induction of oxidative stress. Therefore, to further explore the antioxidant gastroprotective effect of compound SEGA (3a), the activation of caspases (marker for apoptosis) by indomethacin were measured in presence or absence of compound SEGA (3a). The results indicate that compound SEGA (3a) prevents indomethacin-induced activation of caspase-3 (FIG. 14A) in dose dependent manner. Interestingly, compound SEGA (3a) also prevents the activation of caspase-9 during indomethacin treatment (FIG. 15). The activation of caspase-9 indicates the operation of mitochondrial pathway of apoptosis where the development of mitochondrial oxidative stress plays a vital role. Since compound SEGA (3a) is antioxidant in nature in vivo and prevents the activation of caspase-9 it indicates that the compound may prevent the mitochondrial oxidative stress to offer antiapoptotic effect. By performing TUNEL assay it can conclude that SEGA (3a) prevents the indomethcin-induced apoptosis in vivo (FIG. 14B) as well as in vitro cultured gastric mucosa (FIG. 16).

Figure 17:
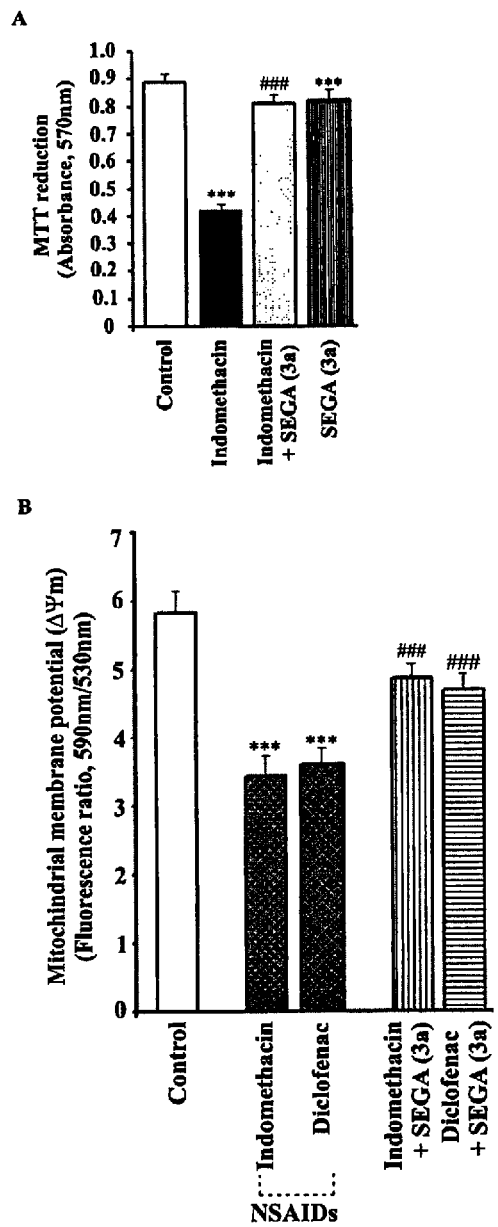
FIG. 17 represents SEGA (3a) protects NSIADs-induced mitochondrial dysfunction. (A) SEGA restores mitochondrial dysfunction as measured by MTT assay as described under "Materials and methods". (B) SEGA protects the indomethacin, diclofenac-induced decrement of membrane potential ($\Delta\psi_m$), as revealed from JC-1 uptake.
Figure 18:
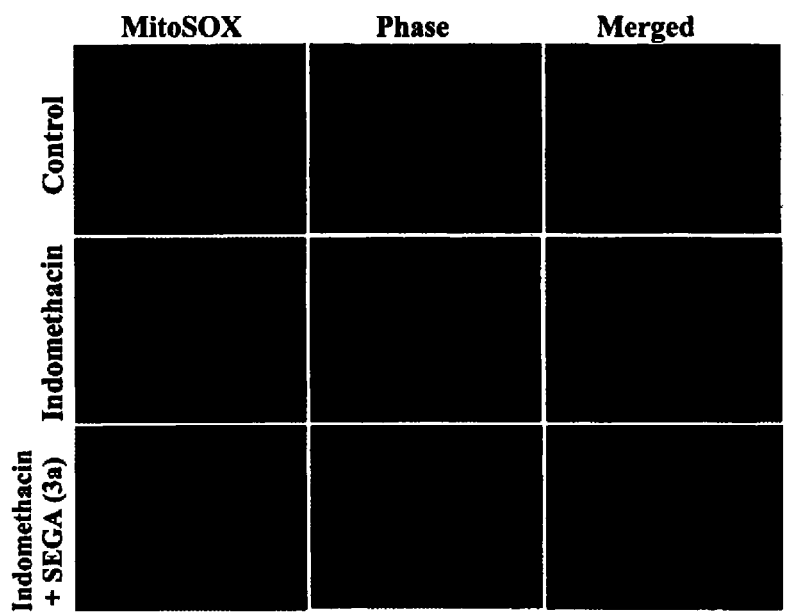
FIG. 18 represents SEGA (3a) scavenges intra mitochondrial superoxide ($O_2^{.-}$) generated by NSAID in vitro. Mitochondrial generation of $O_2^{.-}$ as detected by MitoSOX Red staining of cells from control and indomethacin-treated and SEGA pretreated gastric mucosal cultured cells.
Figure 19:
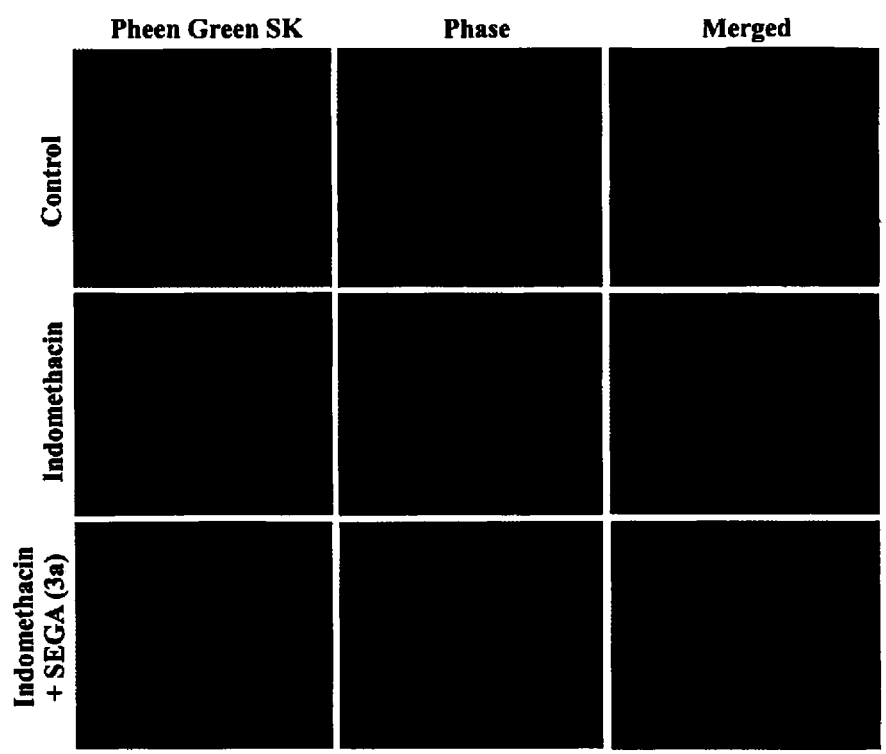
FIG. 19 represents SEGA (3a) free iron chelating property of SEGA (3a) in the in vitro. Generation of free iron as detected by Phen Green SK staining of cells from control and indomethacin-treated and SEGA pretreated gastric mucosal cultured cells.

SEGA (3a) restores the indomethacin induced mitochondrial dysfunction as confirmed by measuring the mitochondrial membrane potential, dehydrogenase activities, and reduces mitochondrial superoxides. NSAIDs (indomethacin, diclofenac) increases the mitochondrial membrane potential as measured by the ratio of fluorescence values at 590 nm (JC-1 aggregate) and 530 nm (JC-1 monomer) (FIG. 17), mitochondrial dehydrogenase activity as measured by MTT reduction assay (FIG. 17) and also increases the superoxides as measured by mitoSOX (FIG. 18) but pretreatment of SEGA (3a) restores all the NSAIDs-induced mitochondrial dysfuctions. SEGA (3a) also chelates the intramitochondrial iron in vitro cultured cell as measured Phen Green SK. (FIG. 19).

EXAMPLES

The following examples are given by way of illustration of the present invention and therefore should not be construed to limit the present invention.

Example 1

General EDC Coupling Procedure for Formation of Esters or Amide

To a solution of 3,4,5-tris(benzyloxy)benzoic acid/4-hydroxy cinnamic acid/Indole-3-aceticacid (1 equiv., 12 mmol), amines (hydrochloride)/alcohol (1.2 equiv., 14.4 mmol), HOBT (1 equiv., 12 mmol, for amines) and $Et_3N$ (6 equiv., 72 mmol, for amines)/DMAP (1 equiv., 12 mmol, for alcohols) in DMF, EDC hydrochloride (1.2 equiv., 14.4 mmol) was added at 0° C. Then the reaction mixture was stirred at room temperature for overnight until completion of reaction, monitored by TLC. After that reaction mixture was quenched by addition of ice cold $H_2O$, and extracted with ethyl acetate. The combined organic phase was washed with brine and dried over $Na_2SO_4$. The organic phase was then reduced under vacuo; the concentrated ethyl acetate extracts were chromatographed over a silica gel column.

Example 2

General Procedure of De Benzylation (Hydrogenolysis)

A mixture of compound and 10% Pd/C (catalytic) in methanol-chloroform mixture (5:1) (10 mL) was hydrogenated at 40 psi for 2 h, filter the solution through celite, after removal of catalyst, the filtrate was evaporated in vacuo to dryness, to give the product.

Example 3

A Process for the Preparation SEGA (3a)

benzyl 3,4,5-tris(benzyloxy)benzoate (1a)

A mixture of gallic acid (4 g, 21.27 mmol), benzyl chloride (19.5 mL, 0.170 mol), tertiary butyl ammonium iodide (catalytic) and $K_2CO_3$ (14.67 g, 106 mmol) in acetone (50 mL) was refluxed for 6 h. The mixture was filtered and the filter cake was washed well with acetone. The combined filtrate and washing solvent were evaporated to dryness in vacuo. The residue was dissolved in ethyl acetate (50 mL), washed with $H_2O$ (20×2 mL) and brine (30 mL), dried over $Na_2SO_4$ and evaporated to dryness. The crude residue was purified by silica gel column chromatography using 5% ethyl acetate in hexane as eluent to obtain pure 1a as white solid (9.01 g, 80%).

$R_f$: 0.512 (15% ethyl acetate in hexane); IR (neat) $v_{max}$ 2963.98, 1707.17, 1595.70; $^1$H NMR (300 MHz, $CDCl_3$) δ 5.12 (s, 6H), 5.32 (s, 2H), 7.25-7.42 (m, 22H); MS (ESI) m/z calcd. for $C_{35}H_{30}O_5$: 530.20. found: 553.01 $[M+Na]^+$.

3,4,5-tris(benzyloxy)benzoic acid (1b)

To a solution of 1a (4 gm, 7.54 mmol) in ethanol (40 mL), 20% KOH solution (10 mL) was added. The reaction mixture was refluxed for 2 h. Ethanol was evaporated under a vacuo, and was neutralized by 6 N HCL. The combined mixture was extracted in EtOAc (3×20 mL), washed with brine solution (20 mL). The organic layer was dried over $Na_2SO_4$ and evaporated to dryness. The crude residue was purified by silica gel column chromatography using 30% ethyl acetate in hexane as eluent to obtain pure compound 3,4,5-tris(benzyloxy)benzoic acid (1b) as white solid (2.78 g, 84%). $R_f$=0.515 (50% ethyl acetate in hexane)

IR (neat) $v_{max}$ 2958.05, 1686.66, 1596.47; $^1$H NMR (300 MHz, $CDCl_3$) δ 5.15 (s, 6H), 7.25-7.44 (m, 17H); MS (ESI) m/z calcd. for $C_{28}H_{24}O_5$: 440.16. found: 463.23 $[M+Na]^+$.

3,4,5-tris(benzyloxy)-N-(2-(5-hydroxy-1H-indol-3-yl)ethyl)benzamide (2a)

2a was synthesized by the condensation of 3,4,5-tris(benzyloxy)benzoic acid (860 mg, 1.95 mmol) and 5-hydroxy tryptamine hydrochloride (496 mg, 2.34 mmol) according using standard EDC coupling method. The compound was isolated as white solid (874 mg, 75%) by elution with 2% methanol in chloroform. $R_f$: 0.470 (5% methanol in chloroform).

$^1$H NMR (300 MHz, $CD_3OD$) δ 3.01 (t, J=6.9 Hz, 2H), 3.64 (t, J=7.05 Hz, 2H), 5.03 (s, 2H), 5.07 (s, 2H), 6.67 (d, J=7.6 Hz, 1H), 6.99 (s, 1H), 7.05 (s, 1H), 7.17 (s, 2H), 7.19-7.46 (m, 16H); $^{13}$C NMR (75 MHz, $CDCl_3$) δ 24.66, 40.61, 71.76 (2C), 74.79, 102.59, 106.14 (2C), 111.78, 123.02, 126.95, 127.26 (6C), 127.57, 127.83, 128.08, 128.18, 128.18 (6C), 129.58, 131.06, 136.35, 137.12, 137.83, 140.25, 140.84, 149.99, 152.25 (2C), 167.31; MS (ESI) m/z calcd. for $C_{38}H_{34}N_2O_5$: 598.24. found: 621.02 $[M+Na]^+$.

3,4,5-trihydroxy-N-(2-(5-hydroxy-M-indol-3-yl) ethyl)benzamide (3a)

3a was prepared by the hydrogenation of 2a and was isolated as slightly reddish colored solid (83%). $R_f$: 0.512 (ethyl acetate); mp: 225-228° C.;

IR (neat) $v_{max}$ 3409.91, 3365.55, 3197.76, 1577.66, 1527.52, 1444.58 $^1$H NMR (300 MHz, $CD_3OD$) δ 2.97 (t, J=7.05 Hz, 2H), 3.60 (t, J=6.9 Hz, 2H), 6.68 (d, J=8.7 Hz, 1H), 6.85 (s, 2H), 7.01 (s, 1H), 7.04 (s, 1H), 7.17 (d, J=8.7 Hz, 1H); $^{13}$C NMR (75 MHz, $CD_3OD$) δ 26.42, 41.78, 103.60, 107.75 (2C), 112.38, 112.62, 112.66, 124.26, 126.33, 129.42, 133.10, 138.07, 146.65 (2C), 151.08, 170.49; HRMS (ESI) m/z $(M+Na)^+$ calcd for $C_{17}H_{16}N_2O_5Na$: 351.0957. found: 351.0948.

Example 4

A Process for the Preparation 2b (E)-N-(2-(5-hydroxy-1H-indol-3-yl)ethyl)-3-(4-hydroxyphenyl)acrylamide (2b) was synthesized according to by the condensation of 4-hydroxy cinnamic acid (150 mg, 0.914 mmol) and 5-hydroxy tryptamine hydrochloride (232 mg, 1.09 mmol) using standard EDC coupling method. 2b was isolated as reddish semi solid (182 mg 62%) by elution with 55% ethyl acetate in hexane. $R_f$: 0.58 (ethyl acetate);

$^1$H NMR (300 MHz, CD$_3$OD) δ 2.93 (t, J=7.35 Hz, 2H), 3.58 (t, J=7.35 Hz, 2H), 6.41 (d, J=15.9 Hz, 1H), 6.68 (dd, J=8.7 Hz, 2.24 Hz, 1H), 6.80 (d, J=8.7 Hz, 2H), 6.83 (d, J=2.1 Hz, 1H), 7.04 (s, 1H), 7.17 (d, J=8.7 Hz, 1H), 7.41 (d, J=8.7 Hz, 2H), 7.47 (d, J=15.6 Hz, 1H); $^{13}$C NMR (75 MHz, CD$_3$OD) δ 26.41, 41.65, 101.15, 112.52, 112.69, 113.12, 116.26 (2C), 118.52, 124.48, 127.52, 129.15, 130.42 (2C), 133.57, 141.62, 154.54, 160.16, 169.60; MS (ESI) m/z calcd. for C$_{19}$H$_{18}$N$_2$O$_3$: 322.13. found: 345.07 [M+Na]$^+$

Example 5

A Process for the Preparation 2c 3-((2-((1H-indol-3-yl) methylamino) ethyl)-1H-indol-5-ol (2c) was synthesized by the condensation of 5-hydroxy tryptamine hydrochloride (50, 0.235 mmol) and indole-3-acetic acid (293 mg, 1.67 mmol) using standard EDC coupling method and was isolated as yellowish semi solid (301 mg, 62%) by elution with 60% ethyl acetate in hexane. $R_f$: 0.512 (ethyl acetate); $^1$H NMR (300 MHz, CD$_3$OD) δ 2.80 (t, J=6.9 Hz, 2H), 3.43 (t, J=7.05 Hz, 2H), 3.64 (s, 2H), 6.66 (dd, J=8.7 Hz, J=2.1, 1H), 6.70 (s, 1H), 6.90 (s, 1H), 7.00 (t, J=7.35 Hz, 1H), 7.09-7.16 (m, 3H), 7.37 (d, J=7.8 Hz, 1H), 7.47 (d, J=7.8 Hz, 1H); $^{13}$C, NMR (75 MHz, CD$_3$OD), δ, 26.07, 34.12, 41.26, 101.22, 109.33, 112.37, 112.55, 112.67, 112.89, 119.35, 120.13, 122.62, 124.24, 125.03, 128.45, 128.91, 133.26, 138.04, 154.85, 174.75; MS (ESI) m/z calcd. for C$_{20}$H$_{19}$N$_3$O$_2$: 333.14. found: 356.19 [M+Na]$^+$

Example 6

A Process for the Preparation TRGA (3b)

1. The compound N-(2-(1H-indol-3-yl)ethyl)-3,4,5-tris(benzyloxy)benzamide (2d)

2d was synthesized the condensation of 3, 4, 5-tris(benzyloxy)benzoic acid (480 mg, 1.09 mmol) and tryptamine hydrochloride (256 mg, 1.308 mmol) using standard EDC coupling method. 2d was isolated as white solid (482 mg, 76%) by elution with 0.5% methanol in chloroform. $R_f$: 0.538 (1.5% methanol in chloroform); mp: 105-107° C.; IR (neat) $v_{max}$ 3413.77, 1637.45, 1579.59, 1496.66; $^1$H NMR (300 MHz, CDCl$_3$) δ 2.96 (t, J=6.14 Hz, 2H), 3.63 (t, J=6.2 Hz, 2H), 4.89 (s, 4H), 4.96 (s, 2H), 6.08 (bs, 1H), 6.85 (S, 3H), 6.87-7.25 (m 18H), 7.54 (d, J=7.5 Hz, 1H), 8.21 (bs, 1H); $^{13}$C NMR (75 MHz, CDCl$_3$) δ 24.90, 40.65, 71.01 (2C), 75.05, 106.44 (2C), 111.39, 118.48, 119.36, 121.98, 122.30, 126.86, 127.44 (6C), 127.88, 128.09, 128.40 (6C), 128.48, 129.97, 136.33, 136.56 (2C), 137.31, 140.69, 140.92, 152.54 (2C), 167.12; MS (ESI) m/z calcd. for C$_{38}$H$_{34}$N$_2$O$_4$: 582.25. found: 605.07 [M+Na]$^+$.

2. N-(2-(1H-indol-3-yl)ethyl)-3,4,5-trihydroxybenzamide (3b)

N-(2-(1H-indol-3-yl)ethyl)-3,4,5-trihydroxybenzamide, TRGA (3b) was prepared by the hydrogenation of 2d and was isolated as reddish colored semi solid (81%).

$R_f$: 0.489 (ethyl acetate); IR (neat) $v_{max}$ 3443.05, 3323.46, 3230.87, 1649.19, 1556.61; $^1$H NMR (300 MHz, CD$_3$OD) δ 3.04 (t, J=7.35 Hz, 2H), 3.62 (t, J=7.2 Hz, 2H), 6.85 (s, 2H), 6.98-7.12 (m, 3H), 7.34 (d, J=7.4 Hz, 1H), 7.62 (d, J=7.5 Hz, 1H); $^{13}$C NMR (75 MHz, CD$_3$OD) δ 26.29, 41.90, 107.78 (2C), 110.32, 112.18, 119.34, 119.58, 122.28, 123.38, 126.36, 128.19, 137.90, 138.02, 146.57 (2C), 170.34; HRMS (ESI) m/z (M+Na)$^+$ calcd for C$_{17}$H$_{16}$N$_2$O$_4$Na: 335.1008. found: 0.335.1003.

Example 7

A Process for the Preparation 2e (E)-N-(2-(1H-indol-3-yl)ethyl)-3-(4-hydroxyphenyl) acrylamide (2e) was synthesized by the condensation of 4-hydroxy cinnamic acid (150 mg, 0.914 mmol) and tryptamine hydrochloride (215 mg, 1.09 mmol) using standard EDC coupling method. 2e was isolated as yellowish solid (178 mg, 64%) by elution with 45% ethyl acetate in hexane. $R_f$: 0.593 (80% ethyl acetate in hexane); mp: 135-138° C.;

IR (neat) $v_{max}$ 3407.98, 3367.48, 3083.96, 1650.95, 1602.74, 1442.66; $^1$H NMR (300 MHz, CD$_3$OD) δ 3.02 (t, J=7.35 Hz, 2H), 3.60 (t, J=7.2 Hz, 2H), 6.41 (d, J=15.6 Hz, 1H), 6.80 (d, J=8.4 Hz, 1H), 7.01 (t, J=7.35 Hz, 2H), 7.09 (t, J=7.35 Hz, 2H), 7.34 (d, J=8.1 Hz, 1H), 7.41 (d, J=8.1 Hz, 2H), 7.47 (d, J=15.6 Hz, 1H), 7.59 (d, J=8.4 Hz, 1H); $^{13}$C NMR (75 MHz, CD$_3$OD) δ 26.37, 41.59, 112.21, 113.26, 116.68 (2C), 118.52, 119.30, 119.60, 122.31, 123.40, 127.70, 128.74, 130.54 (2C), 138.12, 141.70, 160.43, 169.25; MS (ESI) m/z calcd. for C$_{19}$H$_{18}$N$_2$O$_2$: 306.13. found: 329.12 [M+Na]$^+$

Example 8

A Process for the Preparation 2f

N-((1H-indol-3-yl) methyl)-2-(1H-indol-3-yl)ethanamine (20 was synthesized by the condensation of tryptamine hydrochloride (300 mg, 1.53 mmol) and indole-3-acetic acid (293 mg, 1.67 mmol) using standard EDC coupling method. 2f was isolated as yellowish semi solid (301 mg, 62%) by elution with 50% ethyl acetate in hexane.

$R_f$: 0.484 (90% ethyl acetate in hexane); $^1$H NMR (300 MHz, CD$_3$OD) δ 2.86 (t, J=6.9 Hz, 2H), 3.43 (t, J=7.05 Hz, 2H), 3.62 (s, 2H), 6.76 (s, 1H), 6.94-7.15 (m, 5H), 7.31 (d, J=8.1 Hz, 1H), 7.35 (d, J=8.1 Hz, 1H), 7.47-7.50 (m, 2H); $^{13}$C NMR (75 MHz, CD$_3$OD) δ 26.01, 34.02, 41.31, 106.20, 112.21, 112.40, 112.87, 119.22, 119.35, 119.61, 120.08, 122.29, 122.66, 123.45, 125.07, 128.22, 128.43, 128.60, 138.08, 174.80; MS (ESI) m/z calcd. for C$_{20}$H$_{19}$N$_3$O: 317.15. found: 340.24 [M+Na]$^+$

Example 9

A Process for the Preparation MEGA (3c)

The compound 3, 4, 5-tris(benzyloxy)-N-(2-(5-methoxy-1H-indol-3-yl)ethyl)benzamide (2g)

2g was synthesized by the condensation of 1b (480 mg, 1.09 mmol) and 5-methoxy tryptamine (248 mg, 1.308 mmol)

using standard EDC coupling method and was isolated as white solid (565 mg, 84%) by elution with 0.5% methanol in chloroform. $R_f$: 0.517 (1.6% methanol in chloroform); mp: 125-128° C.;

IR (neat) $\nu_{max}$ 3357.84, 1637.45, 1587.31, 1552.59, 1448.44; $^1$H NMR (300 MHz, CDCl$_3$) δ 3.03 (t, J=7.05 Hz, 2H), 3.61 (t, J=7.05 Hz, 2H), 3.74 (s, 3H), 500 (s, 4H), 5.05 (s, 2H), 6.09 (bs, 1H), 6.85 (d, J=8.4 Hz, 1H), 6.93 (s, 2H), 6.99 (s, 1H), 7.05 (s, 1H), 7.25-7.36 (m, 16H), 8.05 (bs, 1H); $^{13}$C NMR (75 MHz, CDCl$_3$) δ 24.91, 40.74, 55.58, 70.95 (2C), 75.03, 100.12, 106.37 (2C), 112.13, 112.23, 122.98, 137.44, 127.44 (6C), 127.70, 127.87 128.08, 128.38 (6C), 128.46, 129.93, 131.40, 136.52 (2C), 137.27, 140.68, 152.56 (2C), 153.88, 166.97; MS (ESI) m/z calcd. for C$_{39}$H$_{36}$N$_2$O$_5$: 612.26. found: 635.10 [M+Na]$^+$.

3, 4, 5-trihydroxy-N-(2-(5-methoxy-1H-indol-3-yl)ethyl)benzamide, MEGA (3c)

3c was prepared by the hydrogenation of 2g (83%).
$R_f$: 0.481 (90% ethyl acetate in hexane); $^1$H NMR (300 MHz, CD$_3$OD) δ 3.00 (t, J=7.05 Hz, 2H), 3.61 (t, J=7.05 Hz, 2H), 3.76 (s, 3H), 6.75 (d, J=8.7 Hz, 1H), 6.86 (s, 2H), 7.07 (s, 1H), 7.09 (s, 1H), 7.22 (d, J=8.7 Hz, 1H); $^{13}$C NMR (75 MHz, CD$_3$OD) δ 26.26, 42.00, 56.16, 101.24, 107.77 (2C), 112.57, 112.87, 113.24, 124.19, 126.28, 129.02, 133.13, 137.86, 146.55 (2C), 154.77, 170.18. HRMS (ESI) m/z (M+Na)$^+$ calcd for C$_{18}$H$_{18}$N$_2$O$_5$Na: 365.1113. found: 0.365.1110.

Example 10

A Process for the Preparation 2h (E)-3-(4-hydroxyphenyl)-N-(2-(5-methoxy-1H-indol-3-yl)ethyl) acrylamide (2h) was synthesized by the condensation of 4-hydroxy cinnamic acid (150 mg, 0.914 mmol) and 5-methoxy tryptamine (207 mg, 1.09 mmol) using standard EDC coupling method. 2h was isolated as yellowish solid (181 mg, 59%) by elution with 25% ethyl acetate in hexane.
$R_f$: 0.424 (80% ethyl acetate in hexane); $^1$H NMR (300 MHz, CD$_3$OD) δ 2.97 (t, J=6.9 Hz, 2H), 3.58 (t, J=7.05 Hz, 2H), 3.78 (s, 3H), 6.38 (d, J=15.6 Hz, 1H), 6.74-6.81 (m, 3H), 7.06 (d, J=8.7 Hz, 2H), 7.22 (d, J=8.7 Hz, 1H), 7.37 (d, J=8.7 Hz, 2H), 7.47 (d, J=15.9 Hz, 1H); $^{13}$C NMR (75 MHz, CD$_3$OD) δ 26.34, 41.66, 56.25, 101.25, 112.62, 112.89, 113.15, 116.66 (2C), 118.52, 124.18, 127.62, 129.05, 130.52 (2C), 133.27, 141.68, 154.84, 160.36, 169.20; MS (ESI) m/z calcd. for C$_{20}$H$_{20}$N$_2$O$_3$: 336.14. found: 359.07 [M+Na]$^+$ Example 11

A Process for the Preparation 2i

N-((1H-indol-3-yl) methyl)-2-(5-methoxy-1H-indol-3-yl) ethanamine (2i) was synthesized by the condensation of 5-methoxy tryptamine (48 mg, 0.25 mmol) and indole-3-acetic acid (50 mg, 0.28 mmol) using standard EDC coupling method. 2c was isolated as yellowish solid (52 mg 61%) by elution with 50% ethyl acetate in hexane. $R_f$: 0.441 (90% ethyl acetate in hexane);
$^1$H NMR (300 MHz, CD$_3$OD) δ 2.83 (t, J=7.2 Hz, 2H), 3.43 (t, J=7.05 Hz, 2H), 3.62 (s, 2H), 3.77 (s, 3H), 6.73-6.76 (m, 2H), 6.97-7.02 (m, 2H), 7.06 (s, 1H), 7.11 (t, J=7.46 Hz, 1H), 7.20 (d, J=8.7 Hz, 1H), 7.36 (d, J=8.1 Hz, 1H), 7.46 (d, J=7.8 Hz, 1H); $^{13}$C NMR (75 MHz, CD$_3$OD) δ 26.06, 34.02, 41.16, 56.26, 101.22, 109.23, 112.36, 112.53, 112.66, 112.88, 119.33, 120.03, 122.61, 124.23, 125.03, 128.43, 128.90, 133.27, 138.05, 154.86, 174.75; MS (ESI) m/z calcd. for C$_{21}$H$_{21}$N$_3$O$_2$: 347.16. found: 370.28 [M+Na]$^+$ Example 12

A Process for the Preparation 4d

Tert-butyl 2-(5-hydroxy-M-indol-3-yl)ethylcarbamate (4a)

To a solution of 5-hydroxy tryptamine hydrochloride (500 mg, 2.35 mmol) in chloroform (10 mL), Sodium bicarbonate (197 mg, 2.35 mmol) water (6 mL), sodium chloride (500 mg), and di-tert-butyloxycarbonyl anhydride (512 mg, 10 mmol) in 3 mL of chloroform were added subsequently. The mixture was refluxed for 3 h with vigorous stiffing. The aqueous phase was washed once with chloroform; the combined organic phases were washed with water (20 mL) and brine (10 mL) and dried over sodium sulfate. The organic layer was removed under reduced pressure. The crude product was purified by silica gel column chromatography to get 4a. 4a was isolated as solid (621 mg, 95%) by elution with 20% ethyl acetate in hexane.

$R_f$: 0.538 (50% ethyl acetate in hexane); mp: 55-57° C.; $^1$H NMR (300 MHz, CDCl$_3$) δ 1.37 (s, 9H), 2.79 (bs, 2H), 3.34 (bs, 2H), 4.61 (bs, 1H), 5.56 (bs, 1H), 6.72 (dd, J=8.7 Hz, 1.8 Hz, 1H), 6.90 (s, 1H), 6.94 (s, 1H), 7.13 (d, J=8.7 Hz, 1H), 8.16 (bs, 1H); $^{13}$C NMR (75 MHz, CDCl$_3$) δ 25.67, 28.37 (3C) 40.59, 79.47, 103.14, 111.84 (2C), 111.98, 123.11, 127.85, 131.41, 149.69, 156.33; MS (ESI) m/z calcd. for C$_{15}$H$_{20}$N$_2$O$_3$: 276.14. found: 299.14 [M+Na]$^+$.

3-(2-(tert-butoxycarbonyl)ethyl)-1H-indol-5-yl 3, 4, 5-tris(benzyloxy)benzoate (4b)

4b was synthesized by the condensation of 3, 4, 5-tris (benzyloxy)benzoic acid (1b) (340 mg, 0.773 mmol) and tert-butyl 2-(5-hydroxy-1H-indol-3-yl)ethylcarbamate (4a) (256 mg, 0.927 mmol). 4b was isolated as white solid (250 mg, 56%) by elution with 25% ethyl acetate in hexane.

$R_f$: 0.428 (45% ethyl acetate in hexane); $^1$H NMR (300 MHz, CDCl$_3$) δ 1.43 (s, 9H), 2.86 (t, J=7.2 Hz, 2H), 3.42 (bs, 2H), 4.63 (bs, 1H), 4.63 (bs, 1H), 5.18 (s, 6H), 6.77 (d, J=7.5 Hz, 1H), 6.99-7.03 (m, 2H), 7.27 (s, 2H), 7.34-7.47 (m, 16H); $^{13}$C NMR (75 MHz, CDCl$_3$) δ 25.60, 28.34 (3C), 40.58, 71.16 (2C), 75.12, 79.21, 103.04, 109.44 (2C), 110.76, 111.75, 111.89, 112.91, 123.66, 127.52 (6C) 127.97, 128.13, 128.46, 128.50 (6C), 131.36, 134.26, 136.44, 137.22, 142.58, 144.07, 149.76, 152.55 (2C), 156.07, 165.85; MS (ESI) m/z calcd. for C$_{43}$H$_{42}$N$_2$O$_7$: 698.29. found: 721.18 [M+Na]$^+$.

3-(2-(tert-butoxycarbonyl)ethyl)-1H-indol-5-yl 3, 4, 5-trihydroxybenzoate (4c)

34c was prepared by the hydrogenation of 4b and was isolated as colorless semi solid (79%). $R_f$: 0.411 (5% methanol in chloroform);
$^1$H NMR (300 MHz, CD$_3$OD) δ 1.41 (s, 9H), 2.89 (t, J=7.2 Hz, 2H), 3.3 (t, J=7.05 Hz, 2H), 6.89 (dd, J=10.2 Hz, 1.8 Hz, 1H), 7.135 (s, 2H), 7.26 (s, 2H), 7.36 (d, J=10.2 Hz, 1H); $^{13}$C NMR (75 MHz, CD$_3$OD) δ 26.71, 28.73 (3C), 42.56, 79.95, 110.29, 110.53 (2C), 111.67, 112.57, 125.06, 121.15, 129.12, 135.88, 140.25, 145.33, 146.3, 146.60 (2C), 158.47, 168.231; MS (ESI) m/z calcd. for C$_{22}$H$_{24}$N$_2$O$_7$: 428.18. found: 451.06 [M+Na]$^+$

3-(2-aminoethyl)-1H-indol-5-yl 3, 4, 5-trihydroxybenzoate (4d)

To a solution of 4c (50 mg, 0.116 mmol) in $CH_2Cl_2$ (100 µL) at 0° C. 96% formic acid (200 µL) was added drop wise. After 30 min. the cooling bath was removed and stirring continued at room temperature for another 1 h. Formic acid was removed under a vacuo; residue was dissolved in MeOH (1 mL). The pH of the solution was then adjusted to 8 with 30% aqueous $NH_3$, The alcoholic portion was removed under reduced pressure to give 4d. Product was isolated as semi solid (31 mg, 82%).

$^1$H NMR (300 MHz, $D_2O$) δ 2.77 (t, J=6.7 Hz, 2H), 3.01 (t, J=6.6 Hz, 2H)), 6.73 (d, J=8.7 Hz, 1H), 6.94 (s, 2H), 7.08 (bs, 2H), 7.22 (d, J=8.7 Hz, 1H); $^{13}$C NMR (75 MHz, $CDCl_3$) δ 21.93, 38.96, 108.70, 109.39, 109.66 (2C), 111.89, 115.28, 119.13, 124.96, 126.10, 133.82, 138.01, 143.07, 143.85 (2C), 169.94; MS (ESI) m/z calcd. for $C_{17}H_{16}N_2O_5$: 328.10. found: 329.05 $[M+H]^+$

Example 13

A Process for the Preparation 5a

In round bottom flask, melatonin (48 mg, 0.21 mmol) was taken in dry $CH_2Cl_2$ (3 ml). The reaction mixture was cooled to –78° C. by keeping in acetone bath with liquid nitrogen. To this chilled reaction mixture boron tribromide (0.12 ml, 12 mmol) was added dropwise and stirring continued at this temperature for another 1 h. Then the reaction mixture was stirred overnight at room temperature for overnight. Completion of reaction was monitored by TLC; the reaction mixture was quenched by addition of water, and 10% Hcl and extracted with ethyl acetate. The combined organic phases were washed with water (20 mL) and brine (10 mL) and dried over sodium sulfate. The organic layer was removed under reduced pressure. The crude product was purified by silica gel column chromatography to give N-(2-(5-hydroxy-1H-indol-3-yl)ethyl) acetamide (5a). Isolated as reddish colored semi solid (20 mg, 45%), by elution with 6% methanol in chloroform.

$R_f$: 0.451 (10% methanol in chloroform); $^1$H NMR (300 MHz, $CD_3OD$) δ 1.92 (s, 3H) 2.86 (t, J=7.2 Hz, 2H), 3.44 (t, J=7.2 Hz, 2H), 6.67 (dd, J=8.7 Hz, 2.22 Hz, 1H), 6.94 (d, J=2.18 Hz, 1H), 7.01 (s, 1H), 7.16 (d, J=8.5 Hz, 1H); $^{13}$C NMR (75 MHz, $CD_3OD$) δ 21.64, 25.25, 40.45, 102.54, 111.39, 111.54, 111.70, 123.23, 128.48, 132.11, 150.12, 172.32; MS (ESI) m/z calcd. for $C_{12}H_{14}N_2O_2$: 218.10. found: 241.11 $[M+Na]^+$

Example 14

A Process for the Preparation 6c 5-(3-(2-(tert-butoxycarbonyl)ethyl)-1H-indol-5-yloxy)-5-oxopentanoic acid (6a)

To a solution of 4a (235 mg, 0.851 mmol), and DMAP (17.5 mg, 0.143 mmol) in THF (5 mL), $Et_3N$ (179 µL, 1.276 mmol) was added. Glutaric anhydride (126 mg, 1.105 mmol) in 3 mL THF was added slowly drop wise to this solution. The mixture was stirred and refluxed under argon for 4 h. THF was removed under vacuum, 5 mL EtOAc was added, followed by the addition of 10 mL of $H_2O$, the mixture was stirred for 10 minutes. The organic phase was separated and extracted with ethyl acetate (5 mL×3). The combined organic phase was washed with brine (10 mL) and dried over $Na_2SO_4$. The organic layer was removed under reduced pressure. The crude product was purified by silica gel column chromatography to give 6a. Isolated as slightly reddish semi solid (245 mg, 74%). by elution with 45% ethyl acetate in hexane on silica gel.

$R_f$: 0.511 (80% ethyl acetate in hexane); $^1$H NMR (300 MHz, $CDCl_3$) δ 1.42 (s, 9H), 2.09-2.14 (m, 2H), 2.54 (t, J=7.05 Hz, 2H), 2.68 (t, J=7.05 Hz, 2H), 2.88 (bs, 2H), 3.39 (bs, 2H), 4.67 (bs, 1H), 6.87 (d, J=8.4 Hz, 1H), 7.00 (bs, 2H), 7.29 (bs, 1H), 8.24 (bs, 1H); $^{13}$C NMR (75 MHz, $CDCl_3$) δ 19.91, 25.73, 28.31 (3C), 32.83, 33.36, 40.72, 79.26, 110.82, 111.48 (2C), 116.03, 123.38, 127.67, 134.15, 143.95, 156.00, 172.38, 177.30; HRMS (ESI) m/z $[M+Na]^+$ calculated for $C_{20}H_{26}N_2O_6Na$: 413.1689. found: 413.1800.

3-(2-(tert-butoxycarbonyl)ethyl)-1H-indol-5-yl 5-(2-(5-hydroxy-1H-indol-3-yl)ethylamino)-5-oxopentanoate (6b)

To a solution of 1b (187 mg, 0.481 mmol), 5-hydroxy tryptamine hydrochloride (112 mg, 0.528 mmol) and $Et_3N$ (337 µL, 2.40 mmol) in DMF (3 mL) was added EDC hydrochloride (110 mg, 0.528 mmol) at 0° C. The reaction mixture was stirred at room temperature for overnight, the reaction mixture was quenched by addition of ice cold $H_2O$ (5 mL), and extracted with ethyl acetate (2×5 mL). The combined organic phase was washed with brine (5 mL) and dried over $Na_2SO_4$. The organic layer was removed under reduced pressure. The crude product was purified by silica gel column chromatography to yield 6b. Isolated as slightly reddish semi solid (97 mg, 36%). by elution with 55% ethyl acetate in hexane on silica gel.

$R_f$: 0.525 (ethyl acetate); $^1$H NMR (300 MHz, $CD_3OD$) δ 1.43 (s, 9H), 1.97-2.07 (m, 2H), 2.33 (t, J=7.35 Hz, 2H), 2.59 (t, J=7.2 Hz, 2H), 2.99 (bs, 4H), 3.32 (bs, 2H), 3.49 (t, J=7.2 Hz, 2H), 6.68 (dd, J=8.7 Hz, 1.8 Hz, 1H), 6.83 (dd, J=8.7 Hz, 1.8 Hz, 1H), 6.96 (d, J=1.8 Hz, 1H), 7.03 (s, 1H), 7.21-7.18 (m, 2H), 7.27-7.34 (m, 2H); $^{13}$C NMR (75 MHz, $CD_3OD$) δ 20.90, 24.96, 25.36, 27.43 (3C), 32.94, 34.71, 39.87, 41.04, 78.57, 102.20, 110.15, 111.05, 111.19, 111.37, 112.46, 115.10, 122.94, 123.10, 123.70, 127.65, 128.65, 128.10, 131.70, 134.52, 143.70, 157.09, 173.14, 173.78; MS (ESI) m/z calcd. for $C_{30}H_{36}N_4O_6$: 548.26. found: 571.25 $[M+Na]^+$ 3-(2-aminoethyl)-1H-indol-5-yl 5-(2-(5-hydroxy-1H-indol-3-yl)ethylamino)-5-oxopentanoate (6c)

To a solution of 6b (90 mg, 0.164 mmol) in $CH_2Cl_2$ (200 µL) at 0° C., 96% formic acid (400 µL) was added drop wise. After 30 mM the cooling bath was removed and stirring continued at room temperature for another 1 h. Formic acid was removed under a vacuo; residue was dissolved in MeOH (1 mL). The pH of the solution was then adjusted to 8 with 30% aqueous $NH_3$, The alcoholic portion was removed under reduced pressure. 6c was isolated as semi solid (60 mg, 81.66%).

$^1$H NMR (300 MHz, $CD_3OD$) δ 1.95-2.02 (m, 2H), 2.32 (t, J=6.9 Hz, 2H), 2.59 (t, J=6.9 Hz, 2H), 2.89 (t, J=6.9 Hz, 2H), 3.08 (bs, 2H), 3.20 (t, J=6.6 Hz, 2H), 3.49 (t, J=6.6 Hz, 2H), 6.67 (d, J=8.4 Hz, 1H), 6.87 (d, J=8.7 Hz, 1H), 6.96 (s, 1H), 7.03 (s, 1H), 7.17 (d J=8.4 Hz, 1H), 7.247 (s, 1H), 7.30 (s, 1H), 7.38 (d, J=8.1 Hz, 1H); $^{13}$C NMR (75 MHz, $CD_3OD$) δ 22.30, 24.43, 26.35, 34.34, 36.09, 41.11, 41.31, 103.55, 110.68, 111.19, 112.38, 112.50, 112.69, 112.98, 116.98, 124.27, 125.97, 128.35, 129.49, 133.12, 136.17, 145.39, 151.12, 174.52, 175.19; HRMS (ESI) m/z $(M+H)^±$ calcd for $C_{25}H_{28}N_4O_4$: 449.2188. found: 449.2182.

Example 15

Determination of In Vitro Antioxidant Property by Ferric Reducing Antioxidant Power (FRAP) Assay The assay was performed in a 96-well microplate. FRAP reagent was prepared by mixing of 10 ml acetate buffer (200 mM, pH-3.6), 1 ml of 2,4,6-tris(2-pyridyl)-s-triazine (TPTZ) solution (10 mM in 40 mM HCl) and 1 ml of ferric chloride solution (20 mM) in distilled water. For 1 h the mixture was kept in a water bath at 37° C. In 96-well microplates, 25 µL of the compounds under investigation dissolved (in methanol, some compound dissolved in water) at different concentrations in the range 1-25 µM was placed in triplicate and freshly prepared FRAP solution (175 µL) was added to this sample. A micro plate reader monitored the absorbance at 595 nm at different time intervals for up to 150 min. The absorbance of a mixture 175 µL TRAP sol and 25 µL methanol or water was taken which was subtracted from the absorbance of the samples at each time interval to calculate the absorbance change (ΔA). The FRAP value at time interval t (FRAP value$_t$) was calculated according to the formula:

$$\text{FRAP value}_t(M) = (\Delta a_t Fl / \Delta a_t Fe^{2+}) \times 10^{-5}$$

Where $\Delta a_t Fl$ is the absorbance change after the time interval t (6 and 65 min) relative to the tested flavonoid at the concentration of 10 µM and $\Delta a_t Fe^{2+}$ is the absorbance change at the same time interval relative to ferrous sulfate at the same concentration (Pal, C; et al. Free Radic Biol Med, 49(2), 258-267, 2010, Firuzi, O; et al. Biochim. Biophys. Acta 1721: 174-184; 2005).

Example 16

Free Radical Scavenging Activity In Vitro (DPPH Assay)

2,2-Diphenyl-1-Picrylhydrazyl (DPPH) is a stable free radical that can accept hydrogen radical or an electron and become a stable diamagnetic molecule. The antioxidants can scavenge the DPPH by donating hydrogen as visualized by discoloration of the DPPH radical from purple to yellow (Pal, C; et al. Free Radic Biol Med, 49(2), 258-267; 2010, Ben Farhat, M.; et al. J. Agric. Food Chem. 57:10349-10356; 2009, Han, J; et al. Wei Sheng Yan Jiu 38:596-598; 2009). The assay system contained 1 mL of compounds under investigation dissolved (in methanol, some compound dissolved in water) at different concentrations in the range 10-100 µM solution and 4 ml of DPPH (0.15 mM) in methanol (80% in water v/v) and mixed well. It was allowed to stand for 30 min at 27° C. away from light. Ascorbic acid at the same concentration was taken as positive control. The absorbance of the solution was measured spectrophotometrically at 517 nm and from the decrease of absorption; the antioxidant activity of different tryptamine derivatives were determined.

Example 17

Animals and Gastric Damage Induced by Indomethacin and Diclofenac

Sprague-Dwaley rats (180-220 gm) were used for this study. Each group (control or experimental) of animals was maintained at 24±2° C. with 12 hrs lights and dark cycle. The animals were fasted for 24 hrs before the start of experiments. They were provided with water ad libitum to avoid food-induced increased acid secretion and its effect on gastric lesions. Gastric mucosal ulcer was developed by indomethacin as described (Pal, C; et al. Free Radic Biol Med, 49(2), 258-267; 2010, Biswas, K.; et al. J. Biol. Chem. 278:10993-11001; 2003, Bandyopadhyay, U.; et al. Life Sci. 71:2845-2865; 2002). Briefly, all the animals were divided into control, indomethacin and test compound group. Oral administration of indomethacin at a dose of 48 mg kg$^{-1}$ b.w was given to the fasted animals to induce gastric ulcer. In the drug-pretreated groups, the animals were given drug (50, 20, 10, 5, 3, 1 mg kg$^{-1}$ b.w.) intraperitoneally 30 min prior to ulcer induction with indomethacin. Control group received vehicle only but no indomethacin. After 4 hrs of indomethacin treatment, the animals were sacrificed under proper euthanasia and stomachs were collected. The mucosal injury was scored as ulcer index as follows: 0=no pathology; 1=one pinhead ulcer. The sum of the total scores divided by the number of animals gave the ulcer index. All the in vivo studies were done in accordance with the institute animal ethical committee guidelines. To see the effect of SEGA on diclofenac induced gastric mucosal injury, gastric mucosal damage was developed by the oral administration of diclofenac (75 mg kg$^{-1}$) and the rest of the experiment was carried out in a similar way as described for indomethacin. Diclofenac produced pinhead ulcer like indomethacin and the mucosal injury was scored as ulcer index as described above. Ethanol-induced gastric mucosal injury was developed with oral administration of 1 ml of 50% ethanol (Banerjee, R. K. (2002) Life Sci 71, 2845-2865) and after 4 hrs the animals were sacrificed and cold-restrain stress induced mucosal injury was developed by immobilizing the animals at 4° C. for 3.5 hrs (Banerjee, R. K. (2002) Life Sci 71, 2845-2865, (2003) J Biol Chem 278, 10993-11001).

Example 18

Histology

Stomach tissues from the animals of different groups were washed first washed several times with PBS (pH 7.4) and later fixed in 10% buffered formalin for 12 hrs at 25° C. The formalin-fixed tissues were then dehydrated and embedded in paraffin for preparing semi-thin sections (Maity, P.; et al. J. Biol. Chem. 283:14391-14401; 2008). The semi-thin sections were prepared using a microtome and taken over poly-L-lysine coated glass slide for hematoxylene-eosine staining. The stained sections were observed under microscope (Leica DM-2500, Germany) and were documented by high-resolution digital camera.

Example 19

Healing Effect of SEGA on Indomethacin-Induced Gastric Damage

Gastric mucosal injury was first induced with indomethacin treatment at a dose of 48 mg kg$^{-1}$. After 4 hrs of the induction of mucosal injury, some of the animals were divided into two different groups (n=6), i.e., auto healing and SEGA-induced healing. This time point was referred as '0' hr of healing. At this point of time, in the SEGA-induced healing group, SEGA was administered (i.p) at the dose of 50 mg kg$^{-1}$ (this dose was selected from the dose-response curve). The animals, which were not treated with SEGA and received only indomethacin, served as the auto healing group. Starting from 0 hr, the stomach was dissected out from all groups at the intervals of 2 hrs, 4 hrs and 8 hrs respectively for measuring ulcer index as described (Maity, P.; et al. *J. Biol. Chem.* 283:14391-14401; 2008) and histological studies.

Example 20

Isolation of Mitochondria

Commercially available kit (Biochain) was used for the isolation of mitochondria from gastric mucosal cells. In brief, scrapped gastric mucosa was finely minced on ice in a petridish containing mitochondria extraction buffer. Ultra-Turrax T-25 homogenizer was used to homogenize the cells. To remove nuclei and unbroken cells the homogenate was first centrifuged at 800×g for 10 min and then finally subjected to 12000×g for 15 min to get the mitochondrial fraction.

Example 21

Measurement of Mitochondrial Oxidative Stress

Mitochondrial oxidative stress was performed earlier through measurement protein carbonyl formation, lipid peroxidation and measurement of total thiol content (Pal, C; et al. *Free Radic Biol Med*, 49(2), 258-267; 2010, Maity, P.; et al. *J. Biol. Chem.* 284:3058-3068; 2009, Maity, P.; et al. *J. Biol. Chem.* 283:14391-14401; 2008, Maity, P.; et al. *J. Pineal Res.* 46:314-323; 2009).

Mitochondrial oxidative stress was studied earlier through the measurement of mitochondrial total thiol depletion, lipid peroxidation and protein carbonyl formation. In brief, thiol content was measured by its reaction with 5-5'-dithionitrobenzoic acid (DTNB) to yield the yellow chromophore of TNB (thionitrobenzoic acid), which was measured at 412 nm Mitochondrial lipid peroxidation was assayed by adding 1 ml of the mitochondrial fraction in 0.9% normal saline to 2 ml of TBA-TCA mixture (0.375% w/v and 15% w/v, respectively) in 0.25 N HCl and was mixed and boiled for 15 min which was then cooled and after centrifugation, the absorbance of the supernatant was read at 535 nm. Tetraethoxypropane was used as standard. Protein carbonyl was measured by following the standard colorimetric method that measures the binding of dinitrophenylhydrazine (DNP) to the carbonyl group and was quantified by taking the absorbance at 362 nm.

Example 22

Assay of Caspase-9 and Caspase-3 Activities

From cytosolic fraction of gastric mucosal tissues, caspase-9 and caspse-3 activities were measured using commercially available kit (Biovision, Mountain View, Calif., USA and Sigma respectively). In brief, the gastric mucosa was homogenized in caspase lysis buffer (provided with the respective kit). The homogenate was centrifuged at 16,000×g for 15 min. The supernatant was collected and mixed with 50 µl of 2× reaction buffer (provided with the respective kit). This was followed by addition of the substrates: Ac-DEDV-pNA (200 µM final concentration) for caspase-3 and LEHD-pNA (200 µM final concentration) for caspase-9. The mixture was incubated at 37° C. for 1 hr and absorbance was taken at 405 nm (Maity, P.; et al. *J. Biol. Chem.* 284:3058-3068; 2009, Maity, P.; et al. *J. Biol. Chem.* 283:14391-14401; 2008, Maity, P.; et al. *J. Pineal Res.* 46:314-323; 2009).

Example 23

Cell Culture

Gastric mucosal cells were isolated and cultured as described earlier (Pal, C; et al. *Free Radic Biol Med*, 49(2), 258-267; 2010) with slight modification. Mucosa from rat stomach was scraped into HBSS (pH 7.4) containing 100 U/ml penicillin and 100-µg/ml streptomycin. The mucosa was then minced and suspended in HBSS (pH 7.4), containing 0.05% hyaluronidase and 0.1% collagenase type I. The suspension was incubated for 30 min at 37° C. in 5% $CO_2$ environment with shaking and then filtered through a sterile nylon mess. The filtrate was centrifuged at 600×g for 5 min, the cell pellet was washed with HBSS (pH 7.4) and further centrifuged. The pellet was incubated in 5 ml of Hans F-12 media in T25 flask supplemented with 10% fetal bovine serum (FBS) and 100 U/ml penicillin, 100-µg/ml streptomycin and gentamycin. Cells were cultured at 37° C. with 5% $CO_2$ and grown to ~90% confluence before treatment. 90% of the cells, obtained following this protocol, possessed epithelial characteristics.

Example 24

Measurement of Mitochondrial Transmembrane Potential ($\Delta\Psi_m$)

Mitochondrial transmembrane potential ($\Delta\Psi_m$) was measured as described (Maity, P.; et al. *J. Biol. Chem.* 284:3058-3068; 2009, Maity, P.; et al. *J. Biol. Chem.* 283:14391-14401; 2008, Maity, P.; et al. *J. Pineal Res.* 46:314-323; 2009). Mitochondria were isolated from gastric mucosal scraping using Mitoisolation kit (Biochain) as described above. Equal amount of mitochondria (25 µg) from each group (control, indomethacin, diclofenac and SEGA pre-treated indomethacin, diclofenac treated) was taken in 100 µl of JC-1 assay buffer (100 mM MOPS, pH 7.5, containing 550 mM KCl, 50 mM ATP, 50 mM $MgCl_2$, 50 mM sodium succinate, 5 mM EGTA) and were incubated in dark with JC1 (300 nM) for 15 min at 25° C. The fluorescence of each sample was measured in a Hitachi F-7000 fluorescence spectrophtometer (excitation 490 nm, emission 530 nm for JC-1 monomer and emission 590 nm for JC-1 aggregates). $\Delta\Psi m$ was expressed as fluorescence ratio of 590 nm/530 nm.

Example 25

Assay of Mitochondrial Dehydrogenase Activity

Mitochondrial metabolic function was studied by observing the ability of mitochondrial dehydrogenases to reduce MTT ([3-(4,5-dimethylthiazol-2-yl)-2,5-diphenyl tetrazolium bromide]) into formazan dye (Pal, C; et al. *Free Radic Biol Med*, 49(2), 258-267; 2010). Equal number of gastric mucosal primary cultured cells were taken ($10^6$) in each well of a 12 well plate and were divided into three groups control, indomethacin treated (5 mM) and SEGA (50 µM) plus indomethacin (5 mM)-treated. After incubating for 16 hrs, cells were dissociated and centrifuged at 500×g for 5 min and the supernatant was then discarded. Cell pellet was reconstituted in fresh cell culture media. Equal number of cells ($10^5$ cells) in a final volume of 100 µl cell culture media from each group was then taken in 96 well plates in triplicates. MTT (0.1% final concentration) solution was added to each well of both control and experimental groups, mixed well and incubated for 3 hrs at 37° C. in a $CO_2$ incubator. After the incubation, the culture medium was aspirated carefully and the insoluble formazan crystals at the bottom of the well were solubilized with 100 µl of MTT solubilization solution containing 10% Triton X-100 plus 0.1 N HCl in anhydrous isopropanol. The MTT reduction (absorbance of formazan dye) was measured at 570 nm.

Example 26

Measurement of Intra Mitochondrial Superoxide

Isolated mucosal cells from both control and indomethacin-treated cultured gastric mucosa were used for detection of intra mitochondrial superoxide using MitoSOX, an superoxide-sensitive fluorescence probe following the protocol as described in the product catalogue (Maity, P.; et al. *J. Biol. Chem.* 284:3058-3068; 2009). Cells were stained with the respective fluorescent probe in HB SS (pH 7.4) and incubated for 15 min at 37° C. in the dark as described in the manufacture's protocols. After the incubation, cells were washed with HBSS three times and continued for fluorescence microscopy (Leica, DM-2500, Leica Microsystems). Staining of Mito-SOX was visualized using Red filter.

Example 27

Measurement of Free Iron

Isolated mucosal cells from both control and indomethacin-treated cultured gastric mucosa were used for free iron localization using Phen Green SK, an iron-sensitive fluorescence probe following the protocol as described in the product catalogue (Maity, P.; et al. *J. Biol. Chem.* 284:3058-3068; 2009). Cells were first incubated with Phen Green SK (20 µm) for 15 min at 37° C. in the dark. After the incubation, cells were washed with HBSS and used for fluorescence microscopy (Leica, DM-2500, Leica Microsystems). Staining of pheen Green SK was visualized using green filter.

Advantages of the Invention

The synthesized derivatives of the present invention have several advantages.
1. These derivatives can chelate free iron, prevent oxidative stress by scavenging ROS and simultaneously offer anti-apoptotic effect in vitro.
2. These derivatives have the ability to prevent the formation of iron-mediated .OH as well as scavenge ROS in vivo. We have shown that these derivatives can prevent gastric mucosal oxidative stress and gastropathy by preventing ROS-mediated activation of apoptosis in gastric mucosal cells induced by NSAIDs.
3. This invention provides a new small molecule having gastroptotective efficacy and a new strategy for drug discovery in gastropathy

The invention claimed is:
1. A compound of general formula 1

General formula 1

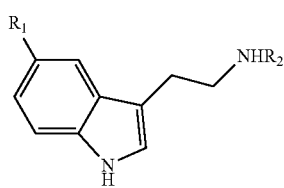

wherein
$R_1$=OH, H, OMe or

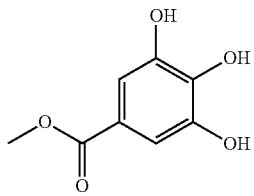

$R_2$=H, or

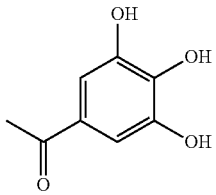

Provided that when $R_2$=H, $R_1$ is always

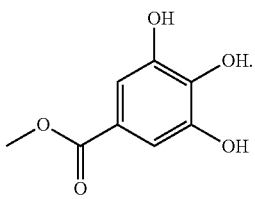

2. The compound of general formula 1 as claimed in claim 1, wherein said compound is selected from the group consisting of:
- 3,4,5-trihydroxy-N-(2-(5-hydroxy-1H-indol-3-yl)ethyl) benzamide SEGA (3a);
- N-(2-(1H-indol-3-yl)ethyl)-3,4,5-trihydroxybenzamide TRGA (3b);
- 3,4,5-trihydroxy-N-(2-(5-methoxy-1H-indol-3-yl)ethyl) benzamide MEGA (3c);
- 3-(2-aminoethyl)-1H-indol-5-yl 3,4,5-trihydroxybenzoate GASA (4d).

3. The compound as claimed in claim 1, wherein ferric reducing antioxidant power (FRAP) value at 6 min, 65 min and absorbance change value in 2,2-Diphenyl-1-Picrylhydrazyl (DPPH) assay are in the range of 14.32±0.36 to 39.51±2.7, 19.65±2.1 to 60.61±7.3 and 0.31±0.06 to 0.449±0.08 respectively.

4. The compounds as claimed in claim 2, wherein compounds of formula SEGA (3a), GASA (4d), TRGA (3b) and MEGA (3c) inhibit an ulcer index value in the range of 30±3 to 61±3.

5. A pharmaceutical composition for the treatment of gastropathy comprising at least one compound of general formula 1 with pharmaceutically acceptable carrier.

6. The pharmaceutical composition as claimed in claim 5, wherein effective amount of compound of general formula 1 is in the range of 1 mg kg$^{-1}$ to 50 mg kg$^{-1}$.

7. The pharmaceutical composition as claimed in claim 5, wherein compound of general formula 1 is administered intraperitoneally.

8. A process for the preparation of compounds of formula SEGA (3a), TRGA (3b), MEGA (3c), and GASA (4d) as claimed in claim 2 comprising the steps of:
i. condensing tryptamine derivatives wherein tryptamine derivatives are selected from the group consisting of serotonin hydrochloride (5-hydroxy tryptamine hydrochloride), tryptamine hydrochloride, 5-methoxy tryptamine, tert butyl 2-(5-hydroxy-1H-indol-3-yl)ethyl carbamate and substituted acid wherein a substituted acid is 3,4,5-tris(benzyloxy) benzoic acid, in the ratio ranging between 1:1.2 to 1:2 using 1-Ethyl-3-(3-dimethylaminopropyl)carbodiimide hydrochloride (EDC hydrochloride) followed by isolating by elution with 2 to 3% methanol in chloroform to obtain compound of formula 2a, 2d, 2g, and 4b;

ii. hydrogenating compound of formula 2a (3,4,5-tris(benzyloxy)-N-(2-(5-hydroxy-1H-indol-3-yl)ethyl)benzamide), 2d (N-(2-(1H-indol-3-yl) ethyl)-3,4,5-tris(benzyloxy) benzamide), 2g (3,4,5-tris (benzyloxy)-N-(2-(5-methoxy-1H-indol-3-yl) ethyl)benzamide) and 4b (3-(2-(tert-butoxycarbonyl) ethyl)-1H-indol-5-yl 3,4,5-tris(benzyloxy)benzoate) to obtain compound of formula SEGA (3a), TRGA (3b), MEGA (3c) and 4c (3-(2-(tert-butoxycarbonyl) ethyl)-1H-indol-5-yl 3, 4,5-trihydroxybenzoate) respectively;

iii. mixing 4c as obtained in step (ii) in 10 to 20% $CH_2Cl_2$ and formic acid at temperature in the range of 0 to 1° C. followed by stirring at temperature in the range of 25 to 27° C. for period in the range of 50 to 80 minutes to obtain GASA (4d).

9. A method for treating gastropathy in an animal comprising administrating the effective amount of at least one compound of general formula 1 according to claim 1.

10. The method as claimed in claim 9, wherein said gastropathy is due to non-steroidal anti-inflammatory drugs (NSAIDs), ethanol and cold-immobilized stress through the development of mitochondrial oxidative stress and subsequent induction of gastric mucosal cell apoptosis.

11. The method as claimed in claim 9, wherein effective amount of compound of general formula 1 is in the range of 1 mg $kg^{-1}$ to 50 mg $kg^{-1}$.

12. The method as claimed in claim 9, wherein compound of general formula 1 is administered intraperitoneally.

13. The method as claimed in claim 9, wherein $ED_{50}$ value for compound SEGA (3a) is in the range of 6 to 8 mg $kg^{-1}$.

14. The method as claimed in claim 9, wherein a compound of formula 1 is a compound of formula SEGA(3a) is a non toxic molecule as established by 3[4,5-dimethylthiazol-2-yl]-2,5-diphenyltetrazolium bromide (MTT) reduction assay.

15. A method for preventing gastric damage in-vitro in cultured gastric mucosa cell comprising administrating the effective amount of at least one compound of general formula 1 according to claim 1.

16. The process as claimed in claim 8, wherein the serotonin hydrochloride (5-hydroxy tryptamine hydrochloride) is reacted with said acid.

17. The process as claimed in claim 8 wherein the compounds exhibit antioxidant properties in vitro.

* * * * *

UNITED STATES PATENT AND TRADEMARK OFFICE
CERTIFICATE OF CORRECTION

PATENT NO. : 8,901,317 B2
APPLICATION NO. : 13/822463
DATED : December 2, 2014
INVENTOR(S) : Uday Bandyopadhyay et al.

It is certified that error appears in the above-identified patent and that said Letters Patent is hereby corrected as shown below:

In the Specification

Column 1, Line 10, "filed Sep. 14, 2009" should be -- filed Sep. 14, 2011 --

Signed and Sealed this
Twenty-third Day of June, 2015

Michelle K. Lee
*Director of the United States Patent and Trademark Office*